United States Patent
Sasaki

(10) Patent No.: US 8,402,812 B2
(45) Date of Patent: Mar. 26, 2013

(54) GAS CONCENTRATION DETECTION APPARATUS

(75) Inventor: Takanori Sasaki, Susono (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 685 days.

(21) Appl. No.: 12/451,647

(22) PCT Filed: Dec. 24, 2008

(86) PCT No.: PCT/JP2008/073916
§ 371 (c)(1),
(2), (4) Date: Nov. 23, 2009

(87) PCT Pub. No.: WO2009/082030
PCT Pub. Date: Jul. 2, 2009

(65) Prior Publication Data
US 2010/0101303 A1    Apr. 29, 2010

(30) Foreign Application Priority Data

Dec. 26, 2007 (JP) ................................ 2007-333494
Mar. 4, 2008 (JP) ................................ 2008-053836

(51) Int. Cl.
*G01N 7/00* (2006.01)
(52) U.S. Cl. ...... 73/23.2; 73/23.31; 73/23.32; 73/31.05; 73/114.72; 73/114.73; 204/431; 204/435
(58) Field of Classification Search .................. 73/23.31, 73/23.32, 31.05, 114.72, 114.73; 204/424–427, 204/431, 435
See application file for complete search history.

(56) References Cited

U.S. PATENT DOCUMENTS

| 6,295,862 B1 * | 10/2001 | Kurokawa et al. ........... 73/31.05 |
| 6,656,337 B2 * | 12/2003 | Kurokawa et al. ........... 204/425 |
| 6,895,800 B2 * | 5/2005 | Tomura et al. ............... 73/23.31 |
| 6,901,785 B2 * | 6/2005 | Tomura et al. ............... 73/31.05 |
| 2002/0179594 A1 | 12/2002 | Hada et al. |
| 2004/0221641 A1 * | 11/2004 | Moritsugu et al. ........... 73/23.31 |

FOREIGN PATENT DOCUMENTS

| EP | 0 995 986 A2 | 4/2000 |
| EP | 1 684 067 A2 | 7/2006 |
| JP | A-2000-137018 | 5/2000 |
| JP | A-2000-171436 | 6/2000 |

(Continued)

OTHER PUBLICATIONS

International Search Report issued on May 6, 2009, in the corresponding International Application No. PCT/JP2008/073916.

(Continued)

*Primary Examiner* — Hezron E Williams
*Assistant Examiner* — Hoang Nguyen
(74) *Attorney, Agent, or Firm* — Oliff & Berridge, PLC

(57) ABSTRACT

It is an object of the present invention to provide a gas concentration detection apparatus that is capable of forming an accurate activity judgment when a gas concentration detection cell begins to detect gas concentration with high accuracy. When warm-up begins at time t0 in a NOx concentration detection apparatus that achieves NOx concentration detection with a NOx sensor cell after excess oxygen is discharged by an oxygen pump cell, a NOx sensor cell output begins to rise at time t1. Subsequently, at time t2, an oxygen pump cell output begins to rise. An inflection point appearing in the NOx sensor cell output is then located. At time t5 at which the inflection point appears, an activity judgment about the NOx sensor cell is formed.

22 Claims, 13 Drawing Sheets

FOREIGN PATENT DOCUMENTS

| | | |
|---|---|---|
| JP | A-2001-74691 | 3/2001 |
| JP | A-2001-141696 | 5/2001 |
| JP | A-2002-116180 | 4/2002 |
| JP | A-2003-50227 | 2/2003 |
| JP | A-2004-177179 | 6/2004 |
| JP | A-2005-91228 | 4/2005 |

OTHER PUBLICATIONS

Written Opinion of the International Searching Authority issued on May 6, 2009, in the corresponding International Application No. PCT/JP2008/073916.

* cited by examiner

GAS CONCENTRATION DETECTION APPARATUS

TECHNICAL FIELD

The present invention relates to a gas concentration detection apparatus, and more particularly to a gas concentration detection apparatus that detects the concentration of a specific gas component in an exhaust gas emitted from an engine.

BACKGROUND ART

There is a known gas concentration detection apparatus having an oxygen pump cell for discharging excess oxygen and a sensor cell for detecting the concentration of a specific component in a gas from which the excess oxygen is discharged (refer, for instance, to Patent Document 1). The gas concentration detection apparatus disclosed in Patent Document 1 corrects the value of a current flowing in the sensor cell in accordance with the value of a current flowing in the oxygen pump cell. This makes it possible to achieve concentration detection with high accuracy even when the concentration of oxygen in a detection target gas varies.

The oxygen pump cell and sensor cell each include an element made of a solid electrolyte. A gas concentration detection apparatus having an element made of such a solid electrolyte needs to raise the temperature of the element to a predefined activity temperature. There is another known apparatus that detects element resistance (element impedance) and exercises heater energization control in accordance with the deviation between the detected element resistance and a target value (refer, for instance, to Patent Document 2). The apparatus disclosed in Patent Document 2 makes it possible to maintain a desired element temperature by correcting the target value for the element resistance in accordance with heater power.

There is still another apparatus that forms an activity judgment about a gas concentration sensor in accordance with element impedance (refer, for instance, to Patent Document 3).

A gas concentration detection apparatus disclosed in Patent Document 6 corrects the value of a current flowing in a sensor cell in accordance with the value of a current flowing in a pump cell when the pump cell discharges excess oxygen from a detection target gas to change the concentration of oxygen in the detection target gas. This makes it possible to avoid an unexpected change in NOx concentration even when the concentration of oxygen in the detection target gas changes.

Patent Document 1:
JP-A-2002-116180
Patent Document 2:
JP-A-2003-50227
Patent Document 3:
JP-A-2004-177179
Patent Document 4:
JP-A-2005-91228
Patent Document 5:
JP-A-2001-141696
Patent Document 6:
JP-A-2000-137018
Patent Document 7:
JP-A-2001-74692
Patent Document 8:
JP-A-2000-171436

DISCLOSURE OF INVENTION

Problem to be Solved by the Invention

In recent years, it has been demanded that the gas concentration sensor be activated early to reduce emissions. However, the element impedance that is used as an index for sensor activity judgment as described in Patent Document 3, for example, varies from one sensor unit to another. Therefore, a sensor activity judgment may not be accurately formed when a gas concentration detection cell begins to detect gas concentration with high accuracy. Further, the gas concentration sensor may not be activated early.

In addition, the value of a current flowing in the gas concentration detection cell varies not only with the discharge of excess oxygen by the oxygen pump cell but also with the oxidation of a gas concentration detection cell electrode. More specifically, when an internal combustion engine is shut down and allowed to stand in the resulting state, the gas concentration detection cell electrode oxidizes as it absorbs oxygen in a measurement target gas. The oxygen combined with the electrode is reduced and desorbed when predefined conditions are established after the start of gas concentration detection cell energization. Therefore, the desorbed oxygen may also cause a current to flow in the gas concentration detection cell, resulting in failure to accurately detect the concentration of a specific gas component in the measurement target gas.

The present invention has been made to solve the above problem. One object of the present invention is to provide a gas concentration detection apparatus that is capable of forming an accurate activity judgment when a gas concentration detection cell begins to detect gas concentration with high accuracy. Another object of the present invention is to provide a gas concentration detection apparatus that is capable of detecting gas concentration with high accuracy without being affected by the oxidation of a gas concentration detection cell electrode.

Means for Solving the Problem

First aspect of the present invention is a gas concentration detection apparatus comprising:

an oxygen pump cell for discharging excess oxygen from a measurement target gas in accordance with voltage application;

a gas concentration detection cell for detecting the concentration of a specific gas component in the gas from which the excess oxygen is discharged by the oxygen pump cell, and outputting a current value according to the detected concentration;

acquisition means which, when the oxygen pump cell and the gas concentration detection cell are being warmed up and when excess oxygen is being discharged, acquires the time at which an inflection point appears in the output of the gas concentration detection cell; and activity judgment means which regards the time acquired by the acquisition means at which the inflection point appears as an activity time of the gas concentration detection cell.

Second aspect of the present invention is the gas concentration detection apparatus according to the first aspect, wherein the acquisition means includes change amount calculation means for calculating the amount of change in the output of the gas concentration detection cell at predetermined time intervals, and acquires, in accordance with a comparison between a reference value and the change amount calculated by the change amount calculation means, the time at which the inflection point appears.

Third aspect of the present invention is the gas concentration detection apparatus according to the first aspect, wherein the acquisition means includes change amount calculation means for calculating the amount of change in the output of the gas concentration detection cell at predetermined time intervals, and acquires, in accordance with a change in the change amount calculated by the change amount calculation means, the time at which the inflection point appears.

Fourth aspect of the present invention is the gas concentration detection apparatus according to the first aspect, wherein the acquisition means acquires the time at which the inflection point appears as the time at which the output of the gas concentration detection cell is equal to or smaller than a reference value.

Fifth aspect of the present invention is the gas concentration detection apparatus according to the first aspect, wherein the oxygen pump cell outputs a current value according to the amount of excess oxygen to be discharged; and wherein the acquisition means considers the correlation between the output of the oxygen pump cell and the output of the gas concentration detection cell, and estimates, in accordance with a change in the output of the oxygen pump cell, the time at which the inflection point appears in the output of the gas concentration detection cell.

Sixth aspect of the present invention is the gas concentration detection apparatus according to the fifth aspect, wherein the acquisition means acquires the time at which an inflection point appears in the output of the oxygen pump cell, and estimates, in accordance with the acquired time, the time at which the inflection point appears in the output of the gas concentration detection cell.

Seventh aspect of the present invention is the gas concentration detection apparatus according to the first aspect, further comprising:

an air-fuel ratio detection cell which outputs a current value according to an air-fuel ratio of the measurement target gas;

wherein the acquisition means considers the correlation between the output of the air-fuel ratio detection cell and the output of the gas concentration detection cell, and estimates, in accordance with a change in the output of the air-fuel ratio detection cell, the time at which an inflection point appears in the output of the gas concentration detection cell.

Eighth aspect of the present invention is the gas concentration detection apparatus according to any one of the first to the seventh aspects, wherein the gas concentration detection cell includes a gas side electrode, which is exposed to the gas from which excess oxygen is discharged by the oxygen pump cell; an atmosphere side electrode, which is exposed to atmospheric air; and an electrolyte layer, which is positioned between the gas side electrode and the atmosphere side electrode to permit the movement of oxygen ions between the electrodes; the gas concentration detection apparatus further comprising:

gas concentration detection means for detecting the concentration of a specific gas component in accordance with the output of the gas concentration detection cell (hereinafter referred to as the cell output) that prevails after the time at which the inflection point appears;

oxidation estimation means for estimating a state of oxidation of the gas side electrode; and correction means for correcting the influence of oxygen reduced from the gas side electrode upon the cell output in accordance with the state of oxidation.

Ninth aspect of the present invention is the gas concentration detection apparatus according to the eighth aspect, further comprising:

gas concentration estimation means for estimating the concentration of a specific gas component in accordance with the operating status of an internal combustion engine;

wherein the correction means corrects the cell output in accordance with the gas concentration that prevails at the inflection point appears and is detected by the gas concentration detection means (hereinafter referred to as the inflection point concentration detection value), with the gas concentration that prevails at the inflection point appears and is estimated by the gas concentration estimation means (hereinafter referred to as the inflection point concentration estimation), and with the oxidation.

Tenth aspect of the present invention is the gas concentration detection apparatus according to the ninth aspect, wherein the correction means includes correction value computation means for computing a correction value in which the influence of the state of oxidation and the elapsed time from the time at which the inflection point appears is reflected in a deviation between the inflection point concentration detection value and the inflection point concentration estimation, and corrects the cell output by subtracting the correction value from the cell output.

Eleventh aspect of the present invention is the gas concentration detection apparatus according to the tenth aspect, wherein the correction value computation means performs computations so that the correction value decreases with an increase in the elapsed time.

Twelfth aspect of the present invention is the gas concentration detection apparatus according to the tenth or the eleventh aspects, wherein the correction value computation means performs computations so that the correction value increases with an increase in the oxidation.

Thirteenth aspect of the present invention is the gas concentration detection apparatus according to any one of the tenth to the twelfth aspects, further comprising:

stability time estimation means for estimating the time at which the gas concentration detection cell detects the cell output on which the influence of oxidation of the gas side electrode is not superimposed (hereinafter referred to as the stability time); and prohibition means for prohibiting the correction means from being executed with respect to the cell output prevailing at the stability time.

Fourteenth aspect of the present invention is the gas concentration detection apparatus according to the thirteenth aspect, wherein the stability time estimation means estimates the stability time as the time at which the correction value is 0 or smaller.

Fifteenth aspect of the present invention is the gas concentration detection apparatus according to any one of the eighth to the fourteenth aspects, wherein the state of oxidation estimated by the oxidation estimation means increases with an increase in the interval between the instant at which the gas concentration detection cell becomes energized and the instant at which the inflection point appears.

Sixteenth aspect of the present invention is the gas concentration detection apparatus according to any one of the eight to the fifteenth aspects, further comprising:

integrated value computation means for computing the integrated value of the cell output that is reached during the interval between the instant at which the gas concentration detection cell becomes energized and the instant at which the inflection point appears;

wherein the state of oxidation estimated by the oxidation estimation means increases with an increase in the integrated value.

Seventeenth aspect of the present invention is the gas concentration detection apparatus according to any one of the eight to the sixteenth aspects, wherein the oxidation estimation means includes air-fuel ratio acquisition means for acquiring the air-fuel ratio of the measurement target gas that prevailed the last time the internal combustion engine shut down; and wherein the state of oxidation estimated by the oxidation estimation means increases with an increase in the leanness of the air-fuel ratio.

Eighteenth aspect of the present invention is the gas concentration detection apparatus according to any one of the eighth to the seventeenth aspects, wherein the oxidation estimation means includes standing time acquisition means for acquiring a standing time, that is, the interval between the last internal combustion engine shutdown and the current internal combustion engine start; and wherein the state of oxidation estimated by the oxidation estimation means increases with an increase in the standing time.

Nineteenth aspect of the present invention is the gas concentration detection apparatus according to any one of the eight to the eighteenth aspects, further comprising:

oxidation inhibition means for inhibiting the oxidation of the gas side electrode during internal combustion engine shutdown.

Twentieth aspect of the present invention is the gas concentration detection apparatus according to the nineteenth aspect, wherein the oxidation inhibition means exercises control to enrich the air-fuel ratio when the internal combustion engine shut down.

Twenty-first aspect of the present invention is a gas concentration detection apparatus comprising:

excess oxygen removal means for removing excess oxygen from a measurement target gas;

a gas concentration detection cell for detecting the concentration of a specific gas component in the gas from which the excess oxygen is removed by the excess oxygen removal means; and activity judgment means which, when the excess oxygen removal means and the gas concentration detection cell are being warmed up and when excess oxygen is being removed, regards the time at which an inflection point appears in the concentration of the specific gas component detected by the gas concentration detection cell as an activity time of the gas concentration detection cell.

Advantages of the Invention

When the oxygen pump cell and the gas concentration detection cell are being warmed up and when excess oxygen is being discharged, the first aspect of the present invention regards the time at which an inflection point appears in the output of the gas concentration detection cell as the activity time of the gas concentration detection cell. This inflection point appears when the oxygen remaining before warm-up is removed. According to the first aspect of the present invention, the gas concentration detection cell is judged to be active when the gas concentration detection cell begins to detect the concentration of a specific gas component without being affected by the remaining oxygen, unlike a common sensor activity (full activity) judgment. This makes it possible to form an accurate activity judgment about the gas concentration detection cell when the gas concentration detection cell begins to detect the concentration of a specific gas component without being affected by the oxygen remaining before warm-up. Consequently, early activation of the gas concentration detection cell can be accomplished to the maximum extent possible.

The second aspect of the present invention calculates the amount of change in the output of the gas concentration detection cell at predetermined time intervals, and locates the inflection point in accordance with a comparison between the reference value and the calculated change amount. This makes it possible to accurately acquire the time at which the gas concentration detection cell begins to detect the concentration of a specific gas component with high accuracy.

The third aspect of the present invention calculates the amount of change in the output of the gas concentration detection cell at predetermined time intervals, and locates the inflection point in accordance with a change in the change amount. This makes it possible to accurately acquire the time at which the gas concentration detection cell begins to detect the concentration of a specific gas component with high accuracy.

The fourth aspect of the present invention acquires the time at which the inflection point appears as the time at which the output of the gas concentration detection cell is equal to or smaller than the reference value. To make the output of the gas concentration detection cell equal to or smaller than the reference value, it is necessary that the oxygen remaining before warm-up be discharged. When the output of the gas concentration detection cell is not greater than the reference value, the gas concentration detection cell can accurately detect the concentration of a specific gas component. This makes it possible to accurately acquire the time at which the gas concentration detection cell begins to detect the concentration of a specific gas component with high accuracy.

The fifth aspect of the present invention considers the correlation between the output of the oxygen pump cell and the output of the gas concentration detection cell, and estimates, in accordance with a change in the output of the oxygen pump cell, the time at which an inflection point appears in the output of the gas concentration detection cell. This makes it possible to accurately estimate the time at which the gas concentration detection cell begins to detect the concentration of a specific gas component with high accuracy.

The sixth aspect of the present invention acquires the time at which an inflection point appears in the output of the oxygen pump cell, and estimates, in accordance with the acquired time, the time at which an inflection point appears in the output of the gas concentration detection cell. Since the inflection point in the output of the oxygen pump cell correlates with the inflection point in the output of the gas concentration detection cell, it is possible to accurately estimate the time at which the gas concentration detection cell begins to detect the concentration of a specific gas component with high accuracy.

The seventh aspect of the present invention considers the correlation between the output of the air-fuel ratio detection cell and the output of the gas concentration detection cell, and estimates, in accordance with a change in the output of the air-fuel ratio detection cell, the time at which an inflection point appears in the output of the gas concentration detection cell. This makes it possible to accurately estimate the time at which the gas concentration detection cell begins to detect the concentration of a specific gas component with high accuracy.

The time at which an inflection point appears in the output of the gas concentration detection cell represents the time at which the excess oxygen remaining in the measurement target gas is discharged by the oxygen pump cell to such an extent that the remaining oxygen no longer affects the output of the gas concentration detection cell. More specifically, the influence of the remaining excess oxygen is eliminated from the output of the gas concentration detection cell after the appearance of the inflection point. If, in this instance, the internal combustion engine in which the gas concentration detection apparatus is mounted is shut down and allowed to stand in the resulting state, the gas side electrode of the gas concentration detection cell oxidizes as it absorbs oxygen in the measurement target gas. The oxygen combined with the gas side electrode is reduced and desorbed when predefined conditions are established after the start of gas concentration detection cell energization. Therefore, the influence of the desorbed oxygen may become superimposed on the output of the gas concentration detection cell, resulting in failure to accurately detect the concentration of a specific gas component even after the appearance of the inflection point in the cell output. The eighth aspect of the present invention estimates the state of oxidation of the gas side electrode of the gas concentration detection cell. In accordance with the estimated state of oxidation, the eighth aspect of the present invention corrects the influence that is exerted on the cell output by the oxygen reduced and desorbed from the gas side electrode. Consequently, the present invention can eliminate the influence of gas side electrode oxidation and accurately detect the concentration of a specific gas component in the measurement target gas.

The ninth aspect of the present invention corrects the output of the gas concentration detection cell in accordance with the gas concentration that prevails at the inflection point and is detected by the gas concentration detection means (inflection point concentration detection value), with the concentration of a specific gas component that prevails at the inflection point and is estimated according to the operating status of the internal combustion engine (inflection point concentration estimation), and with the state of oxidation of the gas side electrode. The time at which the inflection point appears represents the time at which the influence of the excess oxygen remaining in the measurement target gas is eliminated from the output of the gas concentration detection cell. Therefore, the present invention corrects the output of the gas concentration detection cell in accordance with a comparison between the inflection point concentration detection value and inflection point concentration estimation, that is, a concentration comparison made after eliminating the influence of excess oxygen remaining in the measurement target gas. Consequently, the concentration of a specific gas component in the measurement target gas can be accurately detected.

The tenth aspect of the present invention computes a correction value in which the influence of the state of oxidation and the elapsed time from the time at which the inflection point appears is reflected in a deviation between the inflection point concentration detection value and the inflection point concentration estimation, and corrects the cell output by subtracting the correction value from the output of the gas concentration detection cell. Therefore, the present invention can correct the cell output in accordance with the state of oxidation. This makes it possible to effectively correct the influence that is exerted on the cell output by the oxygen that is combined with the gas side electrode due to oxidation reaction.

The eleventh aspect of the present invention performs computations so that the correction value decreases with an increase in the elapsed time from the appearance of the inflection point. The longer the elapsed time, the smaller the influence of gas side electrode oxidation, that is, the influence of oxygen desorbed from the gas side electrode. Therefore, the present invention makes it possible to compute a correction value for effectively eliminating the influence of gas side electrode oxidation.

The twelfth aspect of the present invention performs computations so that the correction value increases with an increase in the state of oxidation. The higher the state of gas side electrode oxidation, the greater the influence of gas side electrode oxidation, that is, the influence of oxygen desorbed from the gas side electrode. Therefore, the present invention makes it possible to compute a correction value for effectively eliminating the influence of gas side electrode oxidation.

The thirteenth aspect of the present invention estimates the time at which the gas concentration detection cell detects the cell output on which the influence of gas side electrode oxidation is not superimposed (stability time), and prohibits the cell output prevailing at the stability time from being corrected. Therefore, the present invention makes it possible to effectively avoid a situation where unnecessary corrections are made to cause an error in the cell output.

The fourteenth aspect of the present invention estimates the stability time as the time at which the correction value is 0 or smaller. The correction value represents a portion of output from the gas concentration detection cell that is affected by gas side electrode oxidation. Therefore, the present invention makes it possible to accurately estimate the stability time in accordance with the correction value.

According to the fifteenth aspect of the present invention, the estimated state of gas side electrode oxidation increases with an increase in the interval between the instant at which the gas concentration detection cell becomes energized and the instant at which a cell output inflection point appears (hereinafter referred to as the "inflection point attainment time"). Here, it can be concluded that the amount of oxygen remaining in the measurement target gas before energization increases with an increase in the inflection point attainment time. In other words, the state of gas side electrode oxidation increases with an increase in the amount of oxygen to which the gas side electrode is exposed before energization. Therefore, the present invention makes it possible to estimate the state of gas side electrode oxidation with high accuracy in accordance with the inflection point attainment time.

The sixteenth aspect of the present invention computes the integrated value of a gas concentration detection cell output that is reached during the inflection point attainment time. The estimated state of gas side electrode oxidation increases with an increase in the integrated value. Here, it can be concluded that the amount of oxygen remaining in the measurement target gas before energization increases with an increase in the integrated value of the cell output, that is, an increase in the state of oxygen pumping in the gas concentration detection cell. The state of gas side electrode oxidation increases with an increase in the amount of oxygen remaining before energization, that is, an increase in the amount of oxygen to which the gas side electrode is exposed before energization. Therefore, the present invention makes it possible to estimate the state of gas side electrode oxidation with high accuracy in accordance with the integrated sensor output value that is reached during the inflection point attainment time.

The seventeenth aspect of the present invention acquires the air-fuel ratio of the measurement target gas that prevails during internal combustion engine shutdown. The estimated state of gas side electrode oxidation increases with an increase in the leanness of the air-fuel ratio. Here, the state of gas side electrode oxidation increases with an increase in the leanness of the air-fuel ratio of the measurement target gas, that is, an increase in the oxygen concentration prevailing around the gas side electrode during internal combustion engine shutdown. Therefore, the present invention makes it possible to estimate the state of gas side electrode oxidation with high accuracy in accordance with the air-fuel ratio of the measurement target gas during internal combustion engine shutdown.

The eighteenth aspect of the present invention acquires the standing time, which is the interval between the last internal combustion engine shutdown and the current internal combustion engine start. The estimated state of gas side electrode oxidation increases with an increase in the standing time. Here, the state of gas side electrode oxidation increases with an increase in the standing time, that is, an increase in the time required for the oxidation reaction of the gas side electrode. Therefore, the present invention makes it possible to estimate the state of gas side electrode oxidation with high accuracy in accordance with the standing time.

The higher the state of gas side electrode oxidation, the greater the extent to which an increase in the accuracy of concentration detection by the gas concentration detection cell is blocked. The nineteenth aspect of the present invention inhibits the oxidation reaction of the gas side electrode during internal combustion engine shutdown. This makes it possible to minimize the influence of gas side electrode oxidation upon the cell output.

The twentieth aspect of the present invention exercises control to enrich the air-fuel ratio when the internal combustion engine shut down. Therefore, the present invention can decrease the concentration of oxygen in the measurement target gas. This makes it possible to effectively inhibit the oxidation of the gas side electrode during internal combustion engine shutdown.

When the excess oxygen removal means and the gas concentration detection cell are being warmed up and when excess oxygen is being removed, the twenty-first aspect of the present invention regards the time at which an inflection point appears in the concentration detected by the gas concentration detection cell as the activity time of the gas concentration detection cell. This inflection point appears when the oxygen remaining before warm-up is removed. According to the twenty-first aspect of the present invention, the gas concentration detection cell is judged to be active when the gas concentration detection cell begins to detect the concentration of a specific gas component without being affected by the remaining oxygen, unlike a common sensor activity (full activity) judgment. This makes it possible to form an accurate activity judgment about the gas concentration detection cell when the gas concentration detection cell begins to detect the concentration of a specific gas component with high accuracy without being affected by the oxygen remaining before warm-up. Consequently, early activation of the gas concentration detection cell can be accomplished to the maximum extent possible.

BEST MODE FOR CARRYING OUT THE INVENTION

Figure 1:
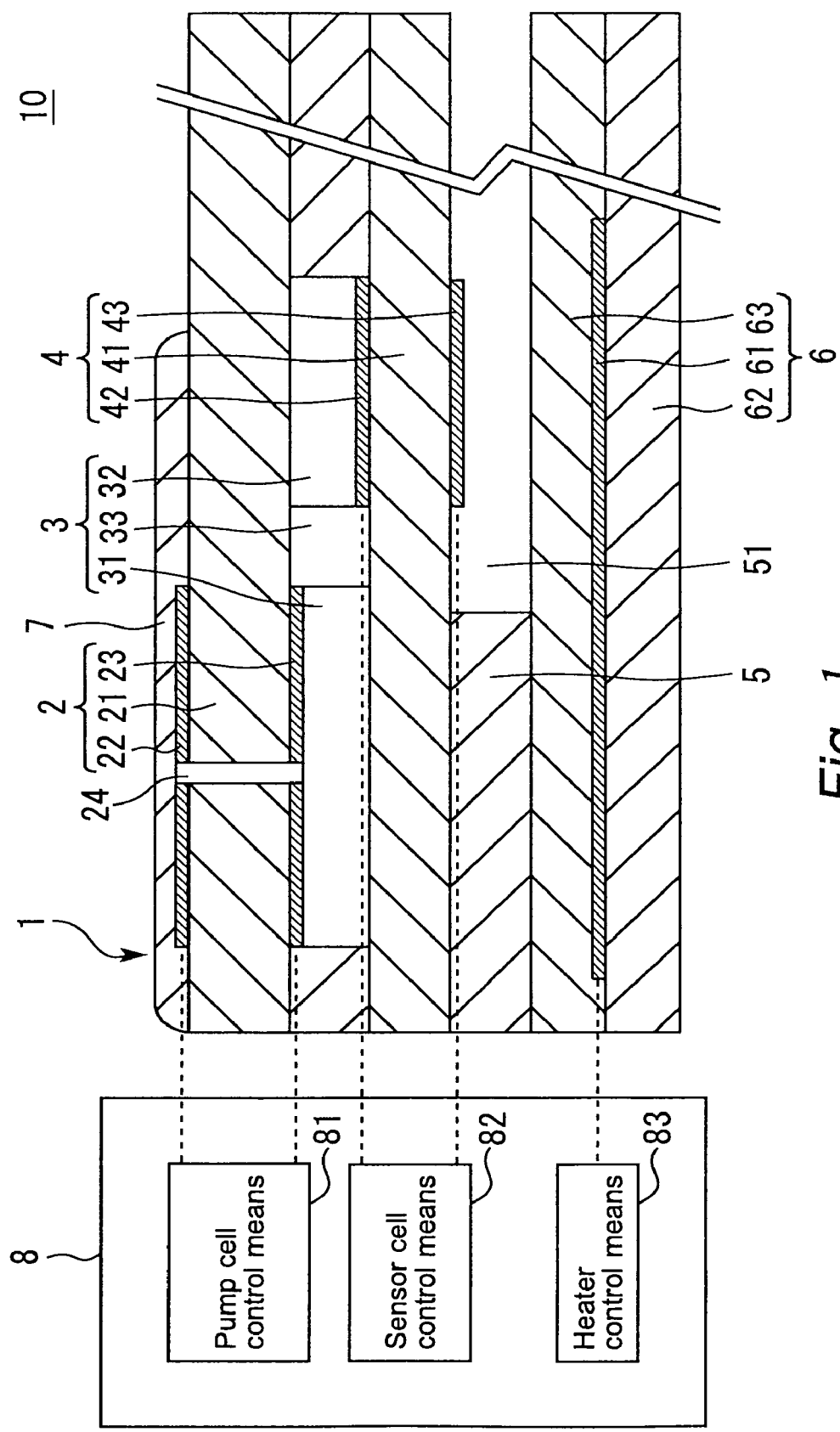
FIG. 1 is a diagram illustrating the configuration of a gas concentration detection apparatus 10 according to a first embodiment of the present invention.

Embodiments of the present invention will now be described with reference to the accompanying drawings. Like elements in the drawings are designated by the same reference numerals and will not be redundantly described. It should be understood that the present invention is not limited to the embodiments described below.

First Embodiment

[Configuration of First Embodiment]

First of all, the configuration of a gas concentration detection apparatus according to a first embodiment of the present invention will be described with reference to FIG. 1. FIG. 1 is a diagram illustrating the configuration of the gas concentration detection apparatus 10 according to the first embodiment. The gas concentration detection apparatus 10 shown in FIG. 1 is a NOx concentration detection apparatus that detects the concentration of a nitrogen oxide (NOx) in an exhaust gas emitted, for instance, from an internal combustion engine (hereinafter referred to as the engine).

The gas concentration detection apparatus 10 includes a NOx sensor 1. The NOx sensor 1 is formed by sequentially stacking a spacer 3, a NOx sensor cell 4, another spacer 5, and a heater 6 under an oxygen pump cell 2.

The oxygen pump cell 2 is capable of removing excess oxygen from a measurement target gas, and includes a solid electrolyte body 21, a first pump electrode 22, and a second pump electrode 23. The solid electrolyte body 21 is sandwiched between the first pump electrode 22 and the second pump electrode 23. The solid electrolyte body 21, which is an element, is oxygen ion conductive. It is shaped like a sheet that is made, for instance, of $ZrO_2$, $HfO_2$, $ThO_2$, and $BiO_3$. The first pump electrode 22 and the second pump electrode 23, which sandwich the solid electrolyte body 21, can be formed, for instance, by a screen printing method.

The first pump electrode 22, which is formed on the front surface of the solid electrolyte body 21, is exposed to a space where the exhaust gas, which is the measurement target gas, exists, that is, exposed to a space within an exhaust path of the engine. For example, a porous cermet electrode containing Pt or other noble metal may be used as the first pump electrode 22.

On the other hand, the second pump electrode 23, which is formed on the back surface of the solid electrolyte body 21 to face the first pump electrode 22, is exposed to a later-described first internal space 31. An electrode inert to a gas containing NOx, such as a porous cermet electrode containing a Pt—Au alloy and zirconia, alumina, or other ceramic material, may be used as the second pump electrode 23.

A pinhole 24 is formed in the oxygen pump cell 2 as an introduction hole that penetrates the solid electrolyte body 21, the first pump electrode 22, and the second pump electrode 23. The diameter of the pinhole 24 is designed so that the exhaust gas to be introduced into the later-described first internal space 31 through the pinhole 24 diffuses at a predetermined rate. Through the pinhole 24 and a later-described porous protective layer 7, the first internal space 31 communicates with a space where the measurement target gas exists.

The porous protective layer 7 is formed on the side toward the first pump electrode 22 of the solid electrolyte body 21 so as to cover the surface of the first pump electrode 22, including the pinhole 24, and its surrounding area. The porous protective layer 7 may be made, for instance, of porous alumina. The porous protective layer 7 makes it possible to not only prevent the first pump electrode 22 from being poisoned, but also prevent the pinhole 24 from being clogged, for instance, by soot contained in the exhaust gas.

The aforementioned first internal space 31 and a second internal space 32 are formed in the spacer 3. The spacer 3 may be made, for instance, of alumina. The two internal spaces 31, 32 communicate with each other through a communication hole 33. The first internal space 31, the second internal space 32, and the communication hole 33 can be formed by making a through hole in the spacer 3.

The NOx sensor cell 4 detects a NOx concentration from the amount of oxygen derived from the reductive decomposition of NOx. The NOx sensor cell 4 includes a solid electrolyte body 41, a first detection electrode 42, and a second detection electrode 43. The solid electrolyte body 41 is sandwiched between the first detection electrode 42 and the second detection electrode 43. The first detection electrode 42 and the second detection electrode 43 can be formed, for instance, by a screen printing method.

The first detection electrode 42, which is formed on the front surface of the solid electrolyte body 41, is exposed to the second internal space 32. For example, a porous cermet electrode containing a Pt—Au alloy and zirconia, alumina, or other ceramic material may be used as the first detection electrode 42.

On the other hand, the second detection electrode 43, which is formed on the back surface of the solid electrolyte body 41 to face the first detection electrode 42, is exposed to a space within an atmosphere duct 51, which is formed in the spacer 5. Atmospheric air is introduced into the atmosphere duct 51. For example, a porous cermet electrode containing Pt or other noble metal may be used as the second detection electrode 43. The atmosphere duct 51 can be formed by making a notch in the spacer 5.

The heater 6 includes sheet-shaped insulation layers 62, 63 and a heater electrode 61, which is buried between the insulation layers 62, 63. The insulation layers 62, 63 are formed, for instance, by a ceramic material such as alumina. The heater electrode 61 is formed, for instance, by a cermet that is made of Pt and alumina or other ceramic material.

The gas concentration detection apparatus 10 according to the first embodiment includes an ECU (Electronic Control Unit) 8, which serves as a control device. The ECU 8 includes pump cell control means 81, sensor cell control means 82, and heater control means 83. The ECU 8 may be provided in addition to an engine control ECU or provided as a part of the engine control ECU.

The pump cell control means 81 is connected to the first pump electrode 22 and the second pump electrode 23, which are included in the oxygen pump cell 2. The pump cell control means 81 applies a voltage between the first pump electrode 22 and the second pump electrode 23, and detects the value of a current flowing in the oxygen pump cell 2 as an "oxygen pump cell output."

The sensor cell control means 82 is connected to the first detection electrode 42 and the second detection electrode 43, which are included in the NOx sensor cell 4. The sensor cell control means 82 applies a voltage between the first detection electrode 42 and the second detection electrode 43 and detects the value of a current flowing in the NOx sensor cell 4 as a "NOx sensor cell output."

The heater control means 83 is connected to the heater electrode 61. The heater control means 83 supplies electrical power to the heater electrode 61.

[Operation of First Embodiment]
(Principles of NOx Concentration Detection)

The principles of NOx concentration detection by the gas concentration detection apparatus 10 will now be described with reference to FIG. 1. Exhaust gas, which is a measurement target gas flowing in the exhaust path of the engine, exists in a space around the porous protective layer 7. The exhaust gas includes, for instance, $O_2$, NOx, $CO_2$, and $H_2O$. The exhaust gas is introduced into the first internal space 31 through the porous protective layer 7 and pinhole 24. The amount of exhaust gas to be introduced into the first internal space 31 is determined by the diffusion resistance of the porous protective layer 7 and pinhole 24.

Before NOx concentration detection, the heater control means 83 first supplies electrical power to the heater electrode 61 to heat the solid electrolyte bodies 21, 41 to their activity temperature. The oxygen pump cell 2 then becomes active so that the pump cell control means 81 applies a voltage between the first pump electrode 22 and the second pump electrode 23. On the second pump electrode 23, which is exposed to the first internal space 31, remaining oxygen and oxygen contained in the exhaust gas are then reduced to oxygen ions $O^{2-}$. The oxygen ions $O^{2-}$ are then pumped out toward the first pump electrode 22 through the solid electrolyte body 21. In this instance, the pump cell control means 81 detects the value of a current flowing in the oxygen pump cell 2 as the oxygen pump cell output. When excess oxygen is discharged by the oxygen pump cell 2, the concentration of oxygen in the exhaust gas decreases to the extent that NOx concentration detection by the NOx sensor cell 4 remains unaffected. Maximizing the voltage applied between the first pump electrode 22 and the second pump electrode 23 makes the pumping operation for oxygen ions $O^{2-}$ more vigorous to increase the amount of oxygen to be discharged.

The exhaust gas from which excess oxygen is removed to decrease the oxygen concentration is introduced into the second internal space 32 through the communication hole 33. When the NOx sensor cell 4 becomes active so that the sensor cell control means 82 applies a voltage between the first detection electrode 42 and the second detection electrode 43, NOx, which is a specific component of the exhaust gas, is decomposed on the first detection electrode 42 to generate oxygen ions $O^{2-}$. More specifically, NOx is first decomposed to NO (converted to a single gas component) and then further decomposed to oxygen ions $O^{2-}$. The oxygen ions $O^{2-}$ pass through the solid electrolyte body 41 and are discharged from the second detection electrode 43 to the atmosphere duct 51. In this instance, the sensor cell control means 82 detects a current flowing in the NOx sensor cell 4 as the NOx sensor cell output, that is, the NOx concentration output for the measurement target gas.

[Features of First Embodiment]

Meanwhile, it is demanded that the NOx sensor 1 be activated early to reduce emissions. More specifically, it is demanded that an activity judgment about the NOx sensor cell 4 for the NOx sensor 1 be formed early to use the NOx sensor cell output for various control operations. To accomplish early activation of the NOx sensor 1, it is important that the status of the NOx sensor 1 be grasped accurately and immediately.

To obtain normal characteristics from the NOx sensor 1 or other NOx sensor that uses an element made of a solid electrolyte body, it is necessary to energize a heater to raise the element temperature to a predefined activity temperature. The apparatus described in Patent Document 3 forms an activity judgment in accordance with element impedance. Another known apparatus forms an activity judgment about a gas concentration sensor in accordance, for instance, with the power supplied to a heater or heater resistance.

However, the element impedance, the power supplied to the heater, and the heater resistance vary from one sensor unit to another (due to individual sensor differences). It is therefore difficult to accurately and immediately grasp the sensor status in accordance, for instance, with element impedance. If a sensor activity judgment is formed early in accordance, for instance, with element impedance, the NOx concentration may be detected after activity judgment while the NOx sensor cell is affected by the remaining oxygen. In other words, the NOx sensor cell output may be low in accuracy although it is generated after activity judgment. This may result in insufficient emission reduction. Further, the use of a method of forming an activity judgment about a gas concentration sensor in accordance, for instance, with element impedance makes it difficult to accomplish early activation of individual sensors to the utmost extent because of individual sensor differences.

Figure 2:
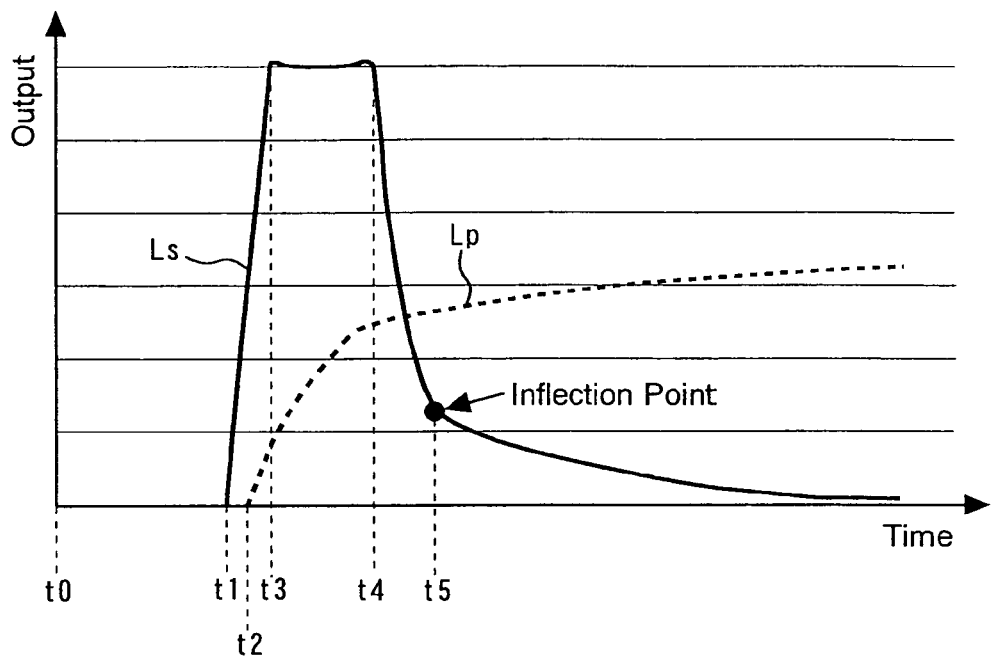
FIG. 2 is a diagram illustrating changes in an oxygen pump cell output and a NOx sensor cell output during NOx sensor warm-up.

In view of the above circumstances, the first embodiment forms an activity judgment about the NOx sensor 1 early and accurately in the manner described below. FIG. 2 is a diagram illustrating how the oxygen pump cell output and NOx sensor cell output change during NOx sensor warm-up. In FIG. 2, a broken line Lp indicates changes in the oxygen pump cell output whereas a solid line Ls indicates changes in the NOx sensor cell output.

At time t0, the NOx sensor 1 begins to warm up at engine start as shown in FIG. 2. More specifically, the heater control means 83 supplies electrical power to the heater electrode 61. As a result of such power application, the temperatures of the oxygen pump cell 2 and NOx sensor cell 4, namely, the temperatures of the solid electrolyte bodies 21, 41 gradually rise. At time t0, oxygen contained in atmospheric air remains in the first internal space 31, which is near the oxygen pump cell 2, and in the second internal space 32, which is near the NOx sensor cell 4. The NOx sensor 1 may warm up not only at engine start but also when recovery is being made from a prolonged fuel cut, which has been performed for a period longer than a predetermined period. It should be noted that the NOx sensor 1 does not always warm up even when recovery is being made from such a prolonged fuel cut.

Subsequently, when the solid electrolyte body 41 of the NOx sensor cell 4 reaches a predetermined temperature at time t1, a NOx sensor cell output is obtained. After time t1, the NOx sensor cell output increases with an increase in the activity of the NOx sensor cell 4 (solid electrolyte body 41). This is because the oxygen remaining in the second internal space 32, which is near the NOx sensor cell 4, is decomposed on the first detection electrode 42 and not because the NOx introduced into the second internal space 32 is decomposed on the first detection electrode 42. Then, at time t3, the NOx sensor cell output reaches an upper limit value, that is, the upper limit value of oxygen concentration that can be detected by the NOx sensor cell 4.

Meanwhile, when the solid electrolyte body 21 of the oxygen pump cell 2 reaches a predetermined temperature at time t2, which is subsequent to time t1, an oxygen pump cell output is obtained. After time t2, the discharge amount of oxygen remaining in the first internal space 31, which is near the oxygen pump cell 2, increases with an increase in the activity of the oxygen pump cell 2 (solid electrolyte body 21). Therefore, the oxygen pump cell output increases with time.

The amount of oxygen discharged from the first internal space 31 increases with an increase in the activity of the oxygen pump cell 2. Further, the amount of exhaust gas introduced into the first internal space 31 increases with an increase in the activity of the oxygen pump cell 2. This lowers the concentration of oxygen remaining in the first internal space 31 and decreases the amount of oxygen supplied from the first internal space 31 to the second internal space 32. Therefore, the concentration of oxygen remaining in the second internal space 32 gradually decreases with an increase in the activity of the oxygen pump cell 2. As a result, the NOx sensor cell output decreases after time t4.

Subsequently, at time t5 at which the oxygen remaining in the second internal space 32 is substantially removed, an inflection point appears in the NOx sensor output to represent a point at which a curve indicative of the NOx sensor cell output greatly changes. More specifically, the NOx sensor cell output generated before the appearance of the inflection point mainly uses the oxygen remaining in the second internal space 32 to perform an oxygen ion pumping operation. Therefore, the curve indicative of the NOx sensor cell output prevailing during such a period is predominantly affected by the concentration of oxygen in the second internal space 32, that is, the activity of the oxygen pump cell 2.

On the other hand, the NOx sensor cell output generated after the appearance of the inflection point mainly uses the NOx in the second internal space 32 to perform an oxygen ion pumping operation because the remaining oxygen is decreased. Therefore, the curve indicative of the NOx sensor cell output prevailing during such a period is predominantly affected by the concentration of NOx in the second internal space 32, that is, the activity of the NOx sensor cell 4. Consequently, at time t5 at which the inflection point appears, it is possible to recognize that the oxygen remaining in the first and second internal spaces 31, 32 before the warm-up of the NOx sensor 1 is substantially removed. Thus, after time t5 at which the inflection point appears, the NOx sensor cell 4 can accurately detect the NOx concentration without being affected by the remaining oxygen.

As such being the case, the first embodiment forms an activity judgment about the NOx sensor 1 at time t5 at which an inflection point appears in the NOx sensor cell output. It should be noted that the NOx sensor activity judgment according to the present invention differs from a common sensor activity (full activity) judgment. The present invention judges that an "active state" prevails when the detection of a NOx sensor output unaffected by the remaining oxygen begins, that is, when the NOx sensor cell output can be used for various control operations without being affected by the remaining oxygen (the same holds true for later-described embodiments). This makes it possible to form an activity judgment about the NOx sensor 1 when the NOx sensor cell 4 begins to detect the NOx concentration without being affected by the remaining oxygen. Therefore, the demand for early activation of the NOx sensor 1 can be satisfied to the utmost extent.

Figure 3:
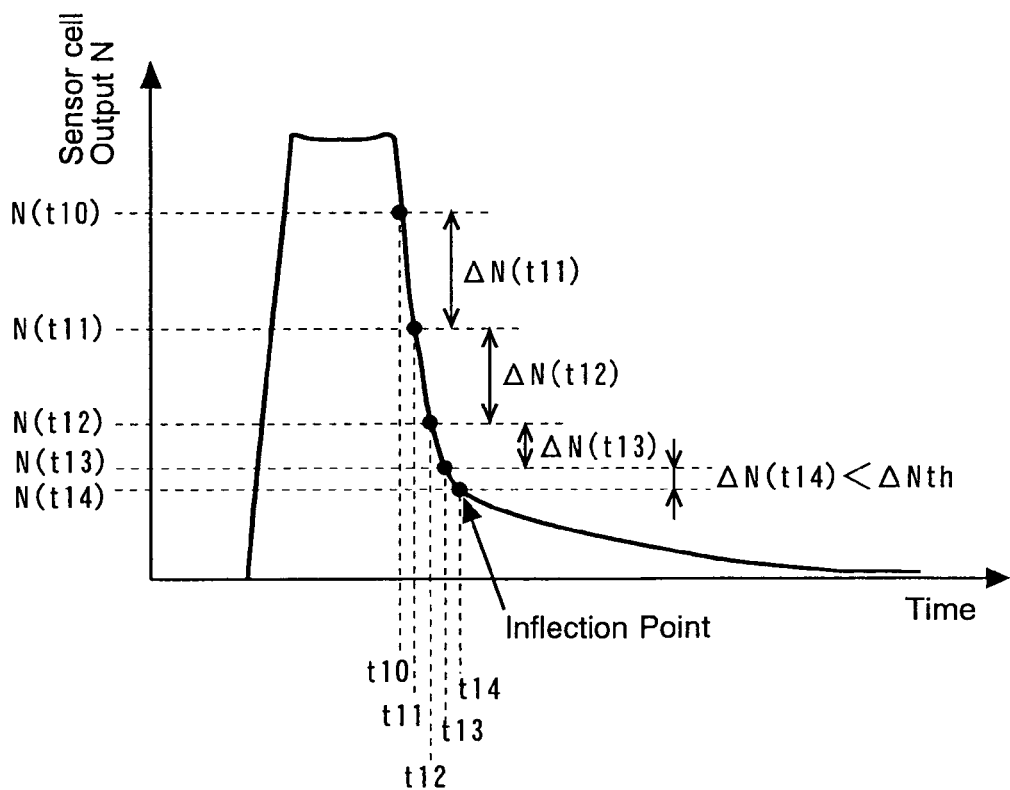
FIG. 3 is a diagram illustrating a first method of locating an inflection point in the NOx sensor cell output.

An operation performed to locate the above-described inflection point will now be described with reference to FIGS. 3 to 5. FIG. 3 is a diagram illustrating a first method of locating the inflection point in the NOx sensor cell output. As shown in the figure, the first step is to acquire the NOx sensor cell output N at predetermined time intervals and calculate a NOx sensor cell output change amount $\Delta N$ upon each NOx sensor cell output acquisition. The amount of change $\Delta N(t)$ at time t can be calculated from Equation (1) below. When the calculated change amount $\Delta N(t)$ is smaller than a predetermined reference value $\Delta Nth$, the NOx sensor cell output $N(t)$ prevailing at time t is identified as an inflection point.

$$\Delta N(t) = N(t-1) - N(t) \qquad (1)$$

The example shown in FIG. 3 indicates that the NOx sensor cell output N decreases during the period between time t10 and time t14. Therefore, the change amounts $\Delta N(t11)-\Delta N(t14)$ calculated from Equation (1) above at time t11, time t12, time t13, and time t14 are all positive values. The change amounts $\Delta N(t11)-\Delta N(t13)$ are not smaller than the predetermined reference value $\Delta Nth$. However, the change amount $\Delta N(t14)$ is smaller than the reference value $\Delta Nth$. Therefore, the NOx sensor cell output $N(t14)$ prevailing at time t14 is identified as an inflection point. Thus, an activity judgment about the NOx sensor 1 is formed at time t14 at which the inflection point appears in the NOx sensor cell output.

Figure 4:
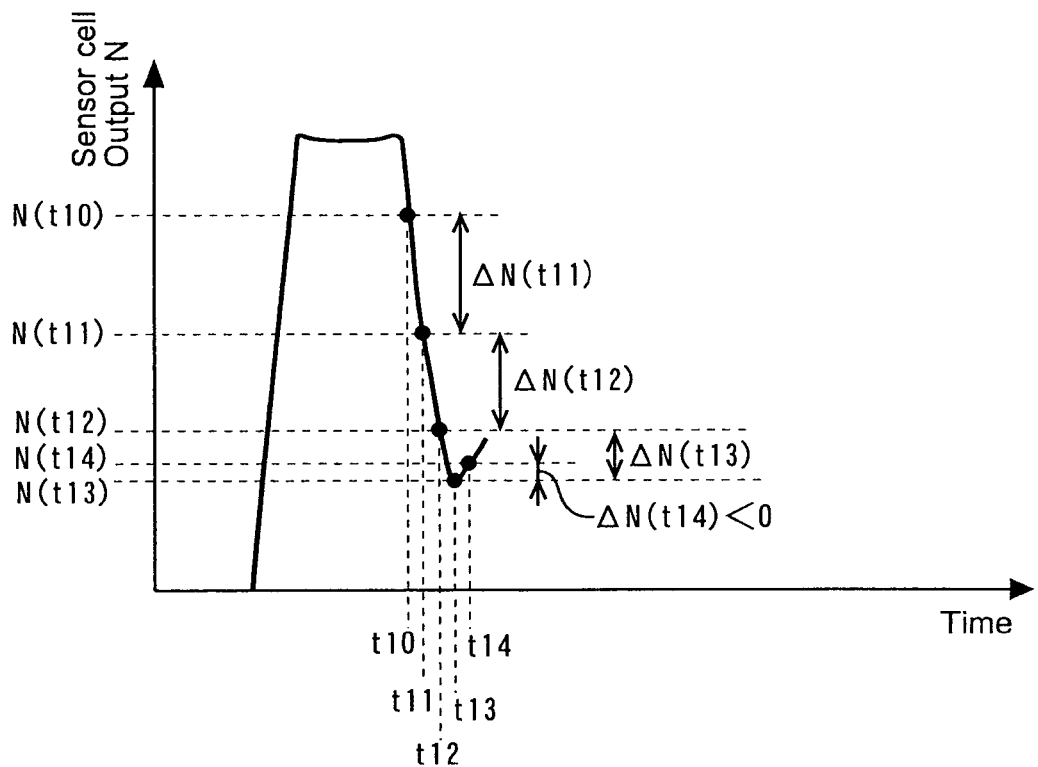
FIG. 4 is a diagram illustrating a second method of locating an inflection point in the NOx sensor cell output.

FIG. 4 is a diagram illustrating a second method of locating an inflection point in the NOx sensor cell output. The example shown in FIG. 4 indicates that the NOx sensor cell output N decreases during the period between time t10 and time t13. After time t13, on the other hand, the NOx sensor cell output N increases. The change amounts $\Delta N(t11)-\Delta N(t13)$ calculated at time t11, time t12, and time t13 are not smaller than the reference value $\Delta Nth$. In the example shown in FIG. 4, therefore, the NOx sensor cell output N begins to increase before the inflection point shown in FIG. 3 is located. Such a change in the NOx sensor cell output occurs when the concentration of NOx in the exhaust gas increases. In the example shown in FIG. 4, an activity judgment about the NOx sensor 1 can be formed because a NOx concentration increase in the exhaust gas after time t13 is detected by the NOx sensor cell 4. Here, the NOx sensor cell output $N(t14)$ at time t14 is greater than the NOx sensor cell output $N(t13)$ at time t13. Therefore, the change amount $\Delta N(t14)$ is a negative value and smaller than the reference value $\Delta Nth$. Thus, the NOx sensor cell output $N(t14)$ at time t14 is regarded as an inflection point. Consequently, an activity judgment about the NOx sensor 1 is formed at time t14.

However, if simply the change amount $\Delta N$ is negative, a rise in the NOx sensor cell output N, which is observed, for instance, between time t1 and time t3 as shown in FIG. 2, may be erroneously identified as an activity of the NOx sensor 1. This error can be avoided by making sure that the last change amount $\Delta N$ (prevailing at the previous time) is positive. In the example shown in FIG. 4, an activity judgment about the NOx sensor 1 is formed at time t14 because the change amount $\Delta N(t13)$ calculated at time t13, which precedes time t14, is positive.

Figure 5:
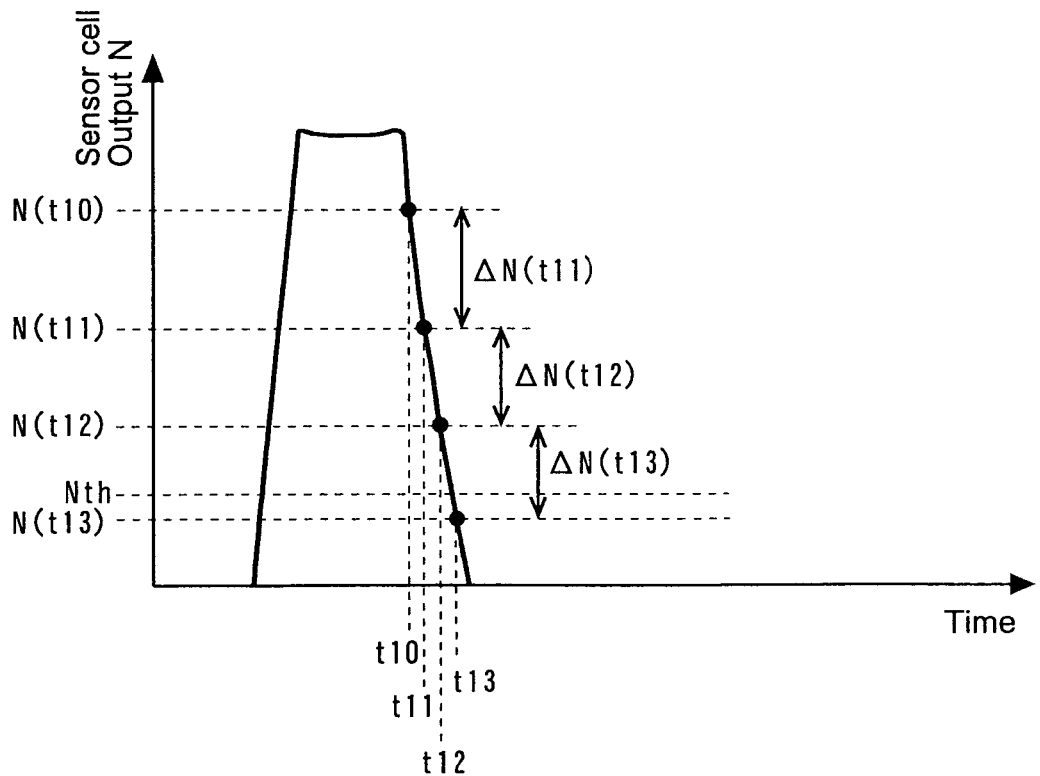
FIG. 5 is a diagram illustrating a third method of locating an inflection point in the NOx sensor cell output.

FIG. 5 is a diagram illustrating a third method of locating an inflection point in the NOx sensor cell output. The example shown in FIG. 5 indicates that the NOx sensor cell output N decreases after time t10. The change amounts $\Delta N(t11)-\Delta N(t13)$ calculated at time t11, time t12, and time t13 are greater than the reference value $\Delta Nth$. In the example shown in FIG. 5, therefore, the NOx sensor cell output N decreases before the inflection point shown in FIG. 3 is located. Such a NOx sensor cell output change occurs when the NOx sensor cell 4 becomes active early. To make the NOx sensor cell output smaller than the reference value $\Delta Nth$, it is necessary that the oxygen remaining before the warm-up of the NOx sensor 1 be removed. When such remaining oxygen is removed, the NOx concentration can be detected while the NOx sensor cell 4 remains unaffected by remaining oxygen. Thus, the NOx sensor cell output $N(t13)$ prevailing at time t13, at which it is smaller than the reference value $\Delta Nth$, is identified as an inflection point. Therefore, an activity judgment about the NOx sensor 1 is formed at time t13.

[Details of Process Performed by First Embodiment]

Figure 6:
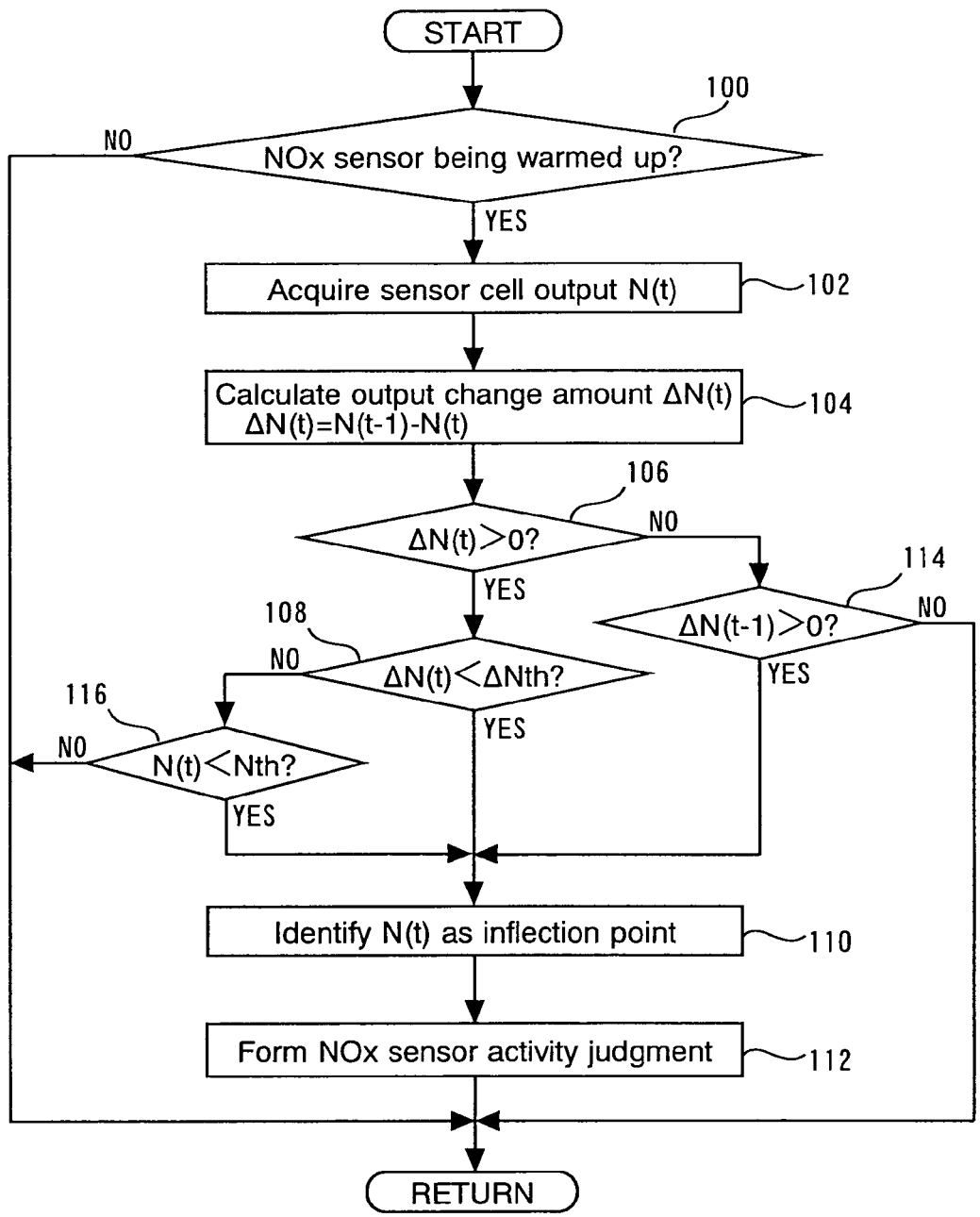
FIG. 6 is a flowchart illustrating a routine that an ECU 8 executes in accordance with the first embodiment of the present invention.

A process performed by the first embodiment will now be described in detail with reference to FIG. 6. FIG. 6 is a flowchart illustrating a routine that the ECU 8 executes in accordance with the first embodiment of the present invention to form an activity judgment about the NOx sensor 1. The routine starts at predetermined intervals. In FIG. 3, the predetermined intervals correspond, for instance, to the interval between time t10 and time t11 and the interval between time t11 and time t12.

First of all, the routine shown in FIG. 6 performs step 100 to judge whether the NOx sensor 1 is warming up. More specifically, step 100 is performed to judge whether the engine is starting to warm up the NOx sensor 1 or whether recovery is being made from a prolonged fuel cut. If the judgment result obtained in step 100 does not indicate that the NOx sensor 1 is warming up, the routine comes to an immediate end because it concludes that the NOx sensor cell output shown in FIG. 2 cannot be obtained.

If, on the other hand, the judgment result obtained in step 100 indicates that the NOx sensor 1 is warming up, the routine proceeds to the next step (step 102) and acquires a NOx sensor cell output $N(t)$. Next, the routine performs step 104 to calculate a change amount $\Delta N(t)$. More specifically, step 104 is performed to compute the change amount $\Delta N(t)$ by substituting the NOx sensor cell output $N(t)$ obtained in step 102 and $N(t-1)$ into Equation (1).

Next, step 106 is performed to judge whether the change amount $\Delta N(t)$ is greater than zero (0). If the judgment result obtained in step 106 indicates that the change amount $\Delta N(t)$ is greater than zero (0), the routine concludes that the currently computed change amount $\Delta N(t)$ is smaller than the change amount $\Delta N(t-1)$ determined by the last routine, then proceeds to the next step (step 108), and judges whether the change amount $\Delta N(t)$ is smaller than the reference value $\Delta Nth$. If the judgment result obtained in step 108 indicates that the change amount ΔN(t) is smaller than the reference value ΔNth, the routine proceeds to the next step (step 110) and identifies the NOx sensor cell output N(t) as an inflection point. In the example shown in FIG. 3, the change amount ΔN(t14) is smaller than the reference value ΔNth; therefore, the NOx sensor cell output N(t14) at time t14 is identified as an inflection point. Then, the routine performs step 112 to conclude that the activity time of the NOx sensor cell 4 is represented by the time at which the inflection point is encountered. Upon completion of step 112, the routine terminates.

If, on the other hand, the judgment result obtained in step 106 does not indicate that the change amount ΔN(t) is greater than zero (0), the routine concludes that the currently computed change amount ΔN(t) is not smaller than the change amount ΔN(t−1) determined by the last routine, then proceeds to the next step (step 114), and judges whether the change amount ΔN(t−1) determined by the last routine greater than zero (0). More specifically, step 114 is performed to judge whether the change amount ΔN(t−2) determined by the second last routine is greater than the change amount ΔN(t−1) determined by the last routine. If the judgment result obtained in step 114 does not indicate that the change amount ΔN(t−1) is greater than zero (0), the NOx sensor cell output N is rising toward the upper limit value. Therefore, the routine concludes that an inflection point is still not encountered, and then comes to an immediate end.

If, on the other hand, the judgment result obtained in step 114 indicates that the change amount ΔN(t−1) is greater than zero (0), the routine concludes that the change amount ΔN(t−2) determined by the second last routine is greater than the change amount ΔN(t−1) determined by the last routine. In this instance, the current routine judges that an increase in the concentration of NOx in the exhaust gas is currently detected, proceeds to step 110, and identifies the NOx sensor cell output N(t) as an inflection point.

If the judgment result obtained in step 108 does not indicate that the change amount ΔN(t) is smaller than the reference value ΔNth, the routine proceeds to the next step (step 116) and judges whether the NOx sensor cell output N(t) is smaller than the reference value ΔNth. If the judgment result obtained in step 116 does not indicate that the NOx sensor cell output N(t) is smaller than the reference value ΔNth, the routine concludes that an inflection point has not appeared in the NOx sensor cell output N, and then comes to an immediate end.

If, on the other hand, the judgment result obtained in step 116 indicates that the NOx sensor cell output N(t) is smaller than the reference value ΔNth, the routine proceeds to step 110 and identifies the NOx sensor cell output N(t) as an inflection point.

As described above, the NOx sensor 1 according to the first embodiment is configured so that the NOx sensor cell 4 detects the NOx concentration after the remaining oxygen is discharged by the oxygen pump cell 2. Therefore, the NOx sensor cell output changes as shown in FIG. 2 while the NOx sensor 1 is warming up. In other words, the NOx sensor cell output changes shown in FIG. 2 result from the difference in the degree of activity (activity difference) between the oxygen pump cell 2 and NOx sensor cell 4. The inflection point appears in the NOx sensor cell output to indicate that the NOx sensor cell 4 can detect the NOx concentration without being affected by the remaining oxygen. In marked contrast to a common sensor activity (full activity) judgment, the first embodiment concludes, when the inflection point appears, that the NOx sensor 1 is active. It means that the first embodiment forms an accurate activity judgment about the NOx sensor 1 in accordance with the inflection point, which appears in the NOx sensor cell output irrespective of individual sensor differences, and not in accordance, for instance, with element impedance, which varies from one sensor unit to another. This makes it possible not only to accomplish early activation of the NOx sensor 1 to the utmost extent, but also to fulfill the demand for emission reduction by using an accurate NOx sensor cell output for various control operations.

In the first embodiment, the oxygen pump cell 2 corresponds to the "excess oxygen removal means" according to the twenty-first aspect of the present invention and the "oxygen pump cell" according to the first aspect of the present invention; and the NOx sensor cell 4 corresponds to the "gas concentration detection cell" according to the first and twenty-first aspects of the present invention.

Further, in the first embodiment, the "change amount calculation means" according to the second and third aspects of the present invention is implemented when the ECU 8 performs step 104; the "acquisition means" according to the second aspect of the present invention is implemented when the ECU 8 performs steps 108 and 110; the "acquisition means" according to the third aspect of the present invention is implemented when the ECU 8 performs steps 106, 114, and 110; and the "acquisition means" according to the fourth aspect of the present invention is implemented when the ECU 8 performs steps 116 and 110.

Second Embodiment

A second embodiment of the present invention will now be described with reference to FIGS. 7 to 9. The gas concentration detection apparatus according to the second embodiment is implemented when the hardware configuration shown in FIG. 1 is employed to let the ECU 8 execute a later-described routine shown in FIG. 9.

[Features of Second Embodiment]

The first embodiment, which has been described earlier, locates an inflection point in accordance, for instance, with a comparison between the NOx sensor cell output change amount ΔN(t) and reference value ΔNth, and forms an activity judgment about the NOx sensor 1 when the inflection point appears.

Meanwhile, the oxygen pump cell 2 is configured the same as the NOx sensor cell 4. These cells output the value of a current that prevails when oxygen ions $O^{2-}$ flow in them. Therefore, there is a correlation between the oxygen pump cell output and NOx sensor cell output. The second embodiment makes use of such a correlation in order to locate an inflection point in the NOx sensor cell output.

Figure 7:
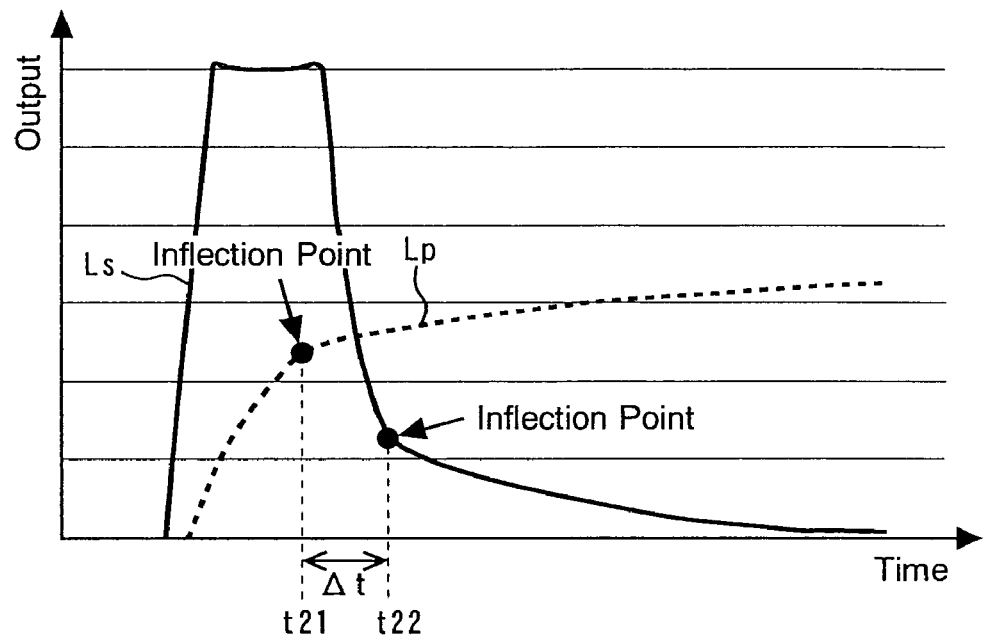
FIG. 7 is a diagram illustrating the correlation between the oxygen pump cell output and NOx sensor cell output during NOx sensor warm-up.

FIG. 7 is a diagram illustrating the correlation between the oxygen pump cell output and NOx sensor cell output during NOx sensor warm-up. In FIG. 7, a broken line Lp indicates changes in the oxygen pump cell output whereas a solid line Ls indicates changes in the NOx sensor cell output.

As shown in FIG. 7, an inflection point appears not only in the NOx sensor cell output but also in the oxygen pump cell output. The inflection point in the oxygen pump cell output appears when the oxygen remaining in the first internal space 31 is discharged. The inventor of the present invention has found that there is a correlation between changes in the oxygen pump cell output and changes in the NOx sensor cell output. More specifically, the inventor of the present invention has found that there is a correlation between time t21, at which an inflection point appears in the oxygen pump cell output, and time t22, at which an inflection point appears in the NOx sensor cell output.

The difference Δtn between time t21 and time t22 can be predetermined, for instance, by an experiment and stored in the ECU 8. Therefore, when the time at which an inflection point appears in the oxygen pump cell output can be determined by a later-described method, the time at which an inflection point appears in the NOx sensor cell output can be estimated by adding the predetermined difference Δtn to the determined time of inflection point appearance in the oxygen pump cell output.

A method of locating an inflection point in the oxygen pump cell output will now be described with reference to FIG. 8. FIG. 8 is a diagram illustrating a method of locating an inflection point in the oxygen pump cell output. The method of locating an inflection point in the NOx sensor cell output, which has been described in conjunction with the first embodiment, can be partially applied to the method of locating an inflection point in the oxygen pump cell output.

First of all, the oxygen pump cell output P is acquired at predetermined intervals. Simultaneously, the amount of change ΔP in the oxygen pump cell output is calculated each time the oxygen pump cell output P is acquired. The amount of change ΔP(t) at time t is calculated from Equation (2) below. When the calculated change amount ΔP(t) is smaller than a predetermined reference value ΔPth, the oxygen pump cell output P(t) prevailing at time t is identified as an inflection point. In Equation (2), the output P(t−1) at time (t−1) is subtracted from the output P(t) at time t so that the change amount ΔP(t) is positive.

$$\Delta P(t) = P(t) - P(t-1) \qquad (2)$$

Figure 8:
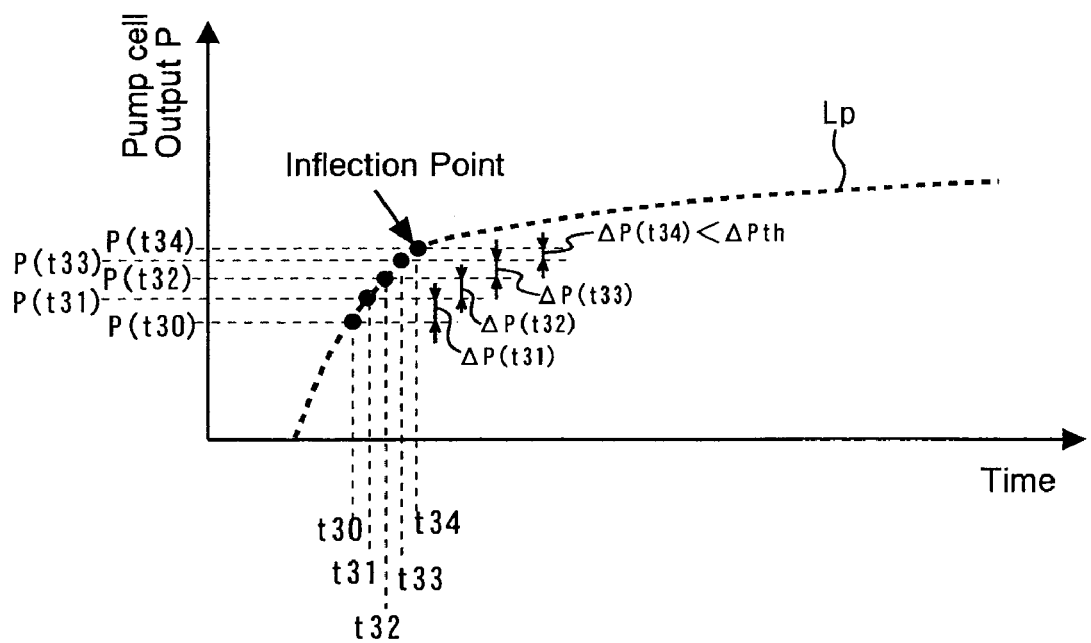
FIG. 8 is a diagram illustrating a method of locating an inflection point in the oxygen pump cell output.

The example shown in FIG. 8 indicates that the oxygen pump cell output P increases during the period between time t30 and time t34. Therefore, the change amounts ΔP(t31)–ΔP(t34) calculated from Equation (2) above at time t31, time t32, time t33, and time t34 are all positive values. The change amounts ΔP(t31)–ΔP(t33) are not smaller than the predetermined reference value ΔPth. However, the change amount ΔP(t34) is smaller than the reference value ΔPth. Therefore, the oxygen pump cell output P(t34) prevailing at time t34 is identified as an inflection point.

Consequently, it can be estimated that an inflection point appears in the NOx sensor cell output N at time (t34+Δtn), which is determined by adding Δtn to time t34 at which an inflection point appears in the oxygen pump cell output. Thus, an activity judgment about the NOx sensor 1 can be formed at time (t34+Δtn).

[Details of Process Performed by Second Embodiment]

Figure 9:
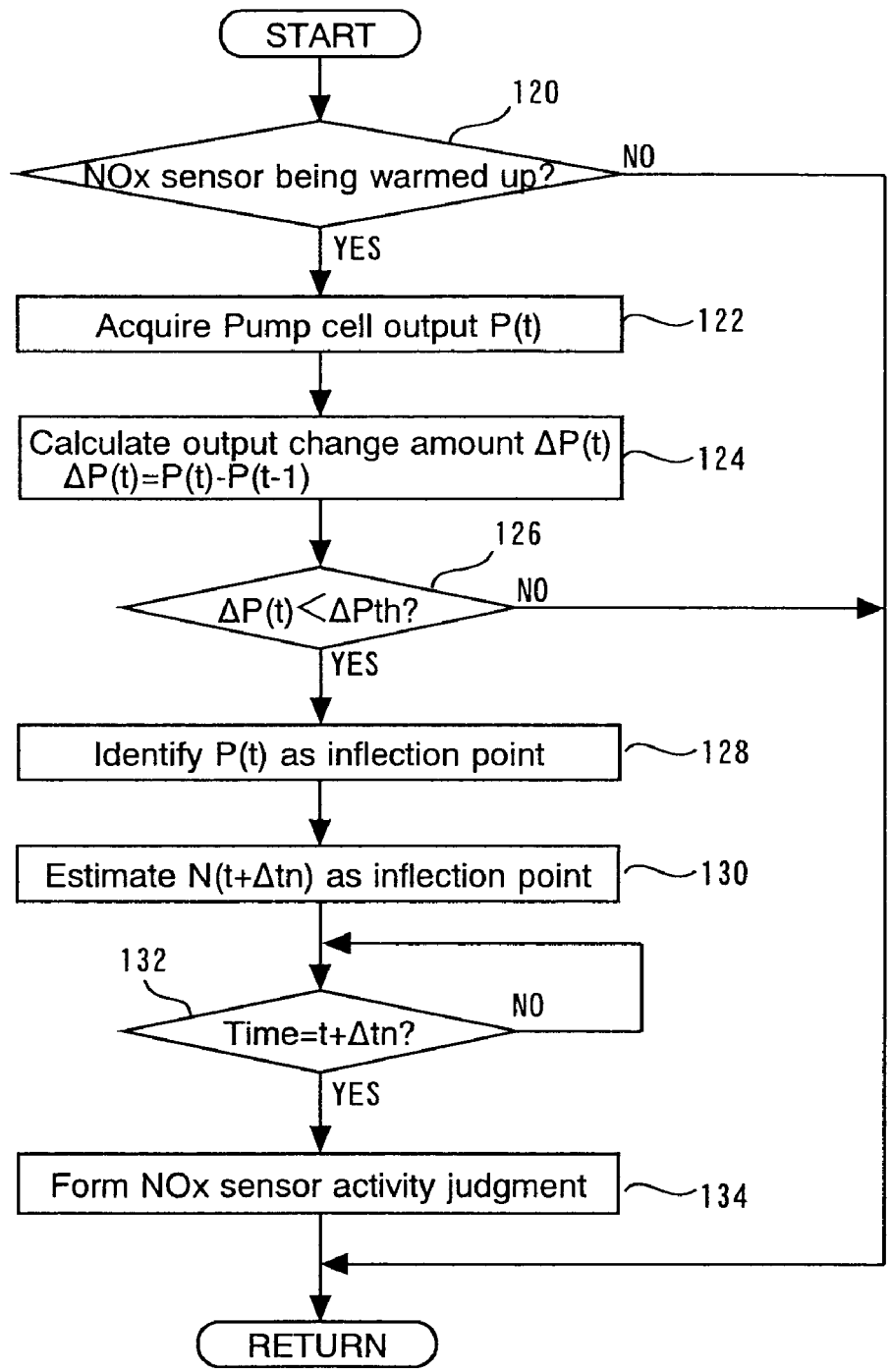
FIG. 9 is a flowchart illustrating a routine that the ECU 8 executes in accordance with a second embodiment of the present invention.

FIG. 9 is a flowchart illustrating a routine that the ECU 8 executes in accordance with the second embodiment of the present invention. The routine starts at predetermined intervals. In FIG. 8, the predetermined intervals correspond, for instance, to the interval between time t30 and time t31.

First of all, the routine shown in FIG. 9 performs step 120 in the same manner as in step 100 of the routine shown in FIG. 6 to judge whether the NOx sensor 1 is warming up. If the judgment result obtained in step 120 does not indicate that the NOx sensor 1 is warming up, the routine terminates because the oxygen pump cell output change shown in FIG. 7 will not be obtained.

If, on the other hand, the judgment result obtained in step 120 indicates that the NOx sensor 1 is warming up, the routine performs step 122 to acquire the oxygen pump cell output P(t). Next, the routine performs step 124 to calculate the change amount ΔP(t) from Equation (2) above by using the oxygen pump cell output P(t) acquired in step 122.

Subsequently, the routine performs step 126 to judge whether the change amount ΔP(t) calculated in step 124 is smaller than the reference value ΔPth. If the judgment result obtained in step 126 indicates that the change amount ΔP(t) is not smaller than the reference value ΔPth, the routine terminates because it concludes that an inflection point has not appeared in the oxygen pump cell output P. If, on the other hand, the judgment result obtained in step 126 indicates that the change amount ΔP(t) is smaller than the reference value ΔPth, the routine performs step 128 to identify the oxygen pump cell output P(t) prevailing at time t as an inflection point.

Next, the routine performs step 130 to estimate the inflection point in the NOx sensor cell output by using the inflection point located in step 128 while considering the correlation between the oxygen pump cell output P and NOx sensor cell output N. Here, as shown in FIG. 7, the time difference Δtn between time t21, at which an inflection point appears in the oxygen pump cell output, and time t22, at which an inflection point appears in the NOx sensor cell output, is predetermined and stored in the ECU 8. In step 130, the routine estimates that an inflection point appears in the NOx sensor cell output at time (t+Δtn), which is obtained by adding the time difference Δtn to time t at which an inflection point appears in the oxygen pump cell output. In other words, it is estimated that the NOx sensor cell output N(t+Δtn) at time (t+Δtn) represents the inflection point.

Subsequently, the routine performs step 132 to judge whether the current time has reached the time (t+Δtn) at which an inflection point appears in the NOx sensor cell output. Step 132 is repeatedly performed until time (t+Δtn) is reached. When the judgment result obtained in step 132 indicates that time (t+Δtn) is reached, the routine estimates that an inflection point has appeared in the NOx sensor cell output. In this instance, the routine performs step 134 in the same manner as in step 112 of the routine shown in FIG. 6 to form an activity judgment about the NOx sensor 1. Upon completion of step 134, the routine terminates.

As described above, the second embodiment determines the time at which an inflection point appears in the oxygen pump cell output P, considers the correlation between the oxygen pump cell output P and NOx sensor cell output N, and estimates the time at which an inflection point appears in the NOx sensor cell output N. This makes it possible to accurately estimate the time at which the NOx sensor cell 4 begins to detect the NOx concentration with high accuracy. Consequently, the second embodiment can accomplish early activation of the NOx sensor 1 to the utmost extent and fulfill the demand for emission reduction, as is the case with the first embodiment.

(Modification)

Figure 10:
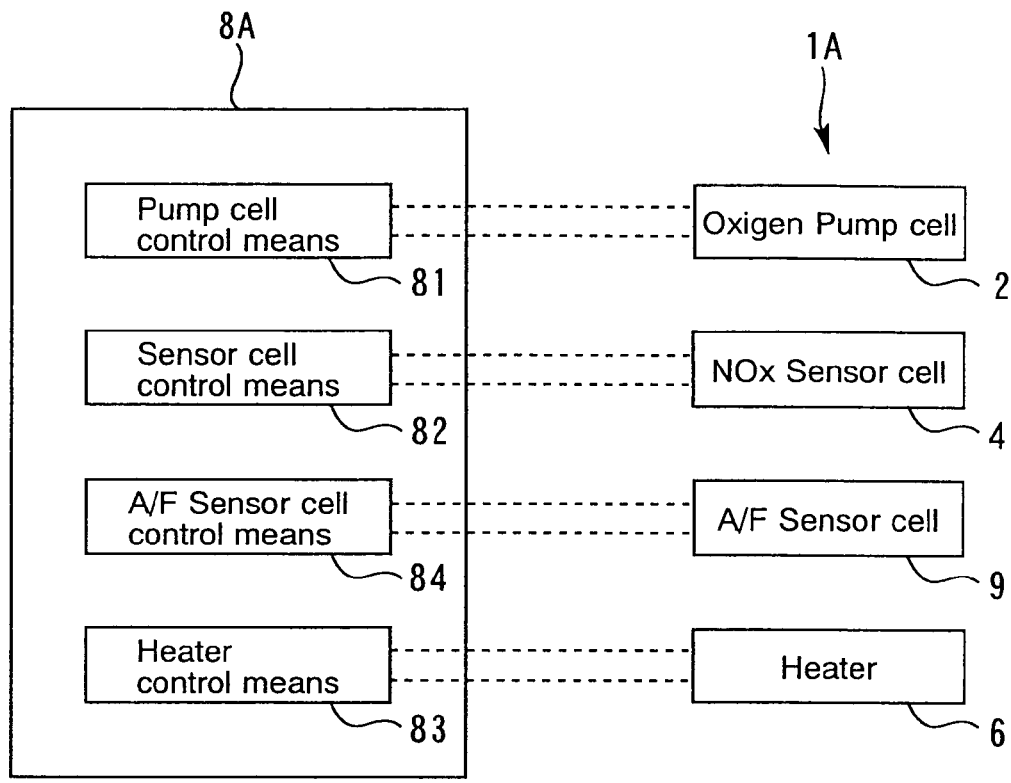
FIG. 10 is a block diagram illustrating essential parts of the gas concentration detection apparatus according to a modification of the second embodiment of the present invention.

A modification of the second embodiment will now be described with reference to FIGS. 10 and 11. The second embodiment, which has been described above, estimates the time at which an inflection point appears in the NOx sensor cell output P while considering the correlation between the oxygen pump cell output P and NOx sensor cell output N. FIG. 10 is a block diagram illustrating essential parts of the gas concentration detection apparatus according to the modification of the second embodiment. The gas concentration detection apparatus shown in FIG. 10 includes a NOx sensor 1A. The NOx sensor 1A is obtained by adding an air-fuel ratio sensor cell 9 to the inside of the NOx sensor 1 shown in FIG. 1. The air-fuel ratio sensor cell 9 includes a solid electrolyte body (not shown), and outputs the value of a current that prevails when oxygen ions $0^{2-}$ flow in the cell. The output of the air-fuel ratio sensor cell 9 is detected by air-fuel ratio sensor cell control means 84, which is included in an ECU 8A. The other portion of the gas concentration detection apparatus will not be described in drawings or in words because it has the same configuration as the gas concentration detection apparatus 10 shown in FIG. 1.

The air-fuel ratio sensor cell 9 and the NOx sensor cell 4 both output the value of a current that prevails when oxygen ions $O^{2-}$ flow in the cells. Therefore, there is a correlation between an air-fuel ratio sensor cell output and the NOx sensor cell output. The modification of the second embodiment uses such a correlation to locate an inflection point in the NOx sensor cell output.

Figure 11:
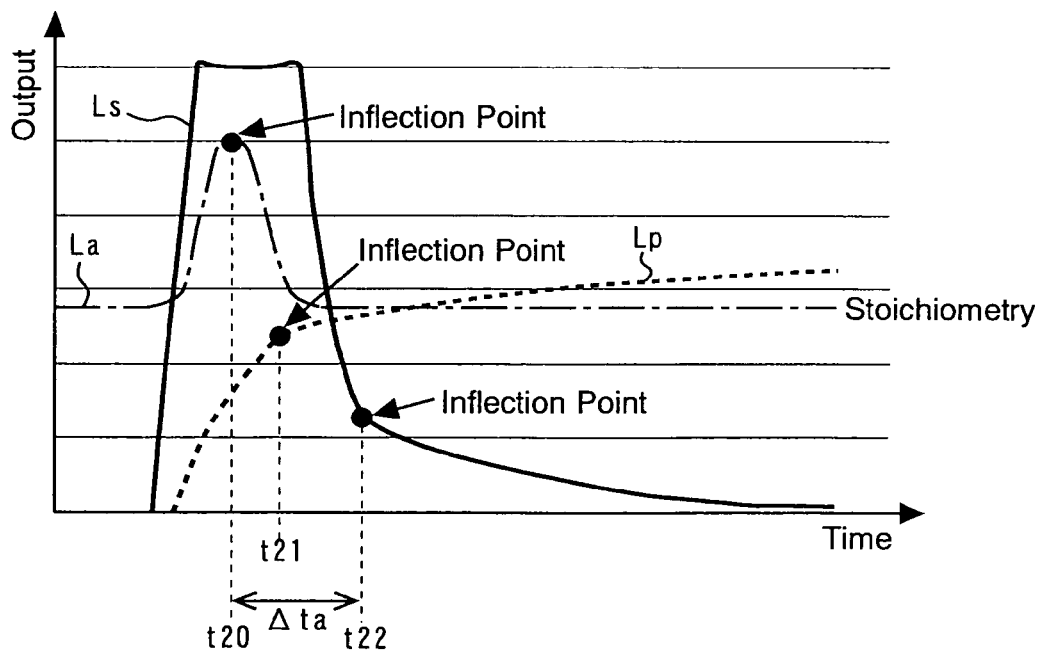
FIG. 11 is a diagram illustrating the correlation between the NOx sensor cell output and an air-fuel ratio sensor cell output during NOx sensor warm-up.

FIG. 11 is a diagram illustrating the correlation between the air-fuel ratio sensor cell output and the NOx sensor cell output during NOx sensor warm-up. In FIG. 11, a one-dot chain line La indicates changes in the air-fuel ratio sensor cell output whereas a solid line Ls indicates changes in the NOx sensor cell output. FIG. 11 also uses a broken line Lp to indicate oxygen pump cell output changes for reference purposes.

As shown in FIG. 11, an inflection point appears not only in the NOx sensor cell output but also in the air-fuel ratio sensor cell output. The inflection point may be defined as an air-fuel ratio sensor cell output that is generated when the amount of change in the air-fuel ratio sensor cell output changes from positive to negative. There is a correlation between time t20, at which an inflection point appears in the air-fuel ratio sensor output, and time t22, at which an inflection point appears in the NOx sensor cell output. The difference Δta between time t20 and time t22 can be predetermined, for instance, by an experiment and stored in the ECU 8. Therefore, when the inflection point in the air-fuel ratio sensor cell output can be located, the time at which an inflection point appears in the NOx sensor cell output can be estimated. Consequently, the modification of the second embodiment makes it possible to accurately estimate the time at which the NOx sensor cell 4 begins to detect the actual NOx concentration with high accuracy, and form an activity judgment about the NOx sensor 1 at the estimated time, as is the case with the second embodiment.

In the modification of the second embodiment, the air-fuel ratio sensor cell 9 corresponds to the "air-fuel ratio detection cell" according to the seventh aspect of the present invention. In the second embodiment, the "acquisition means" according to the fifth and sixth aspects of the present invention is implemented when the ECU 8 performs steps 126, 128, and 130.

Third Embodiment

Figure 12A:
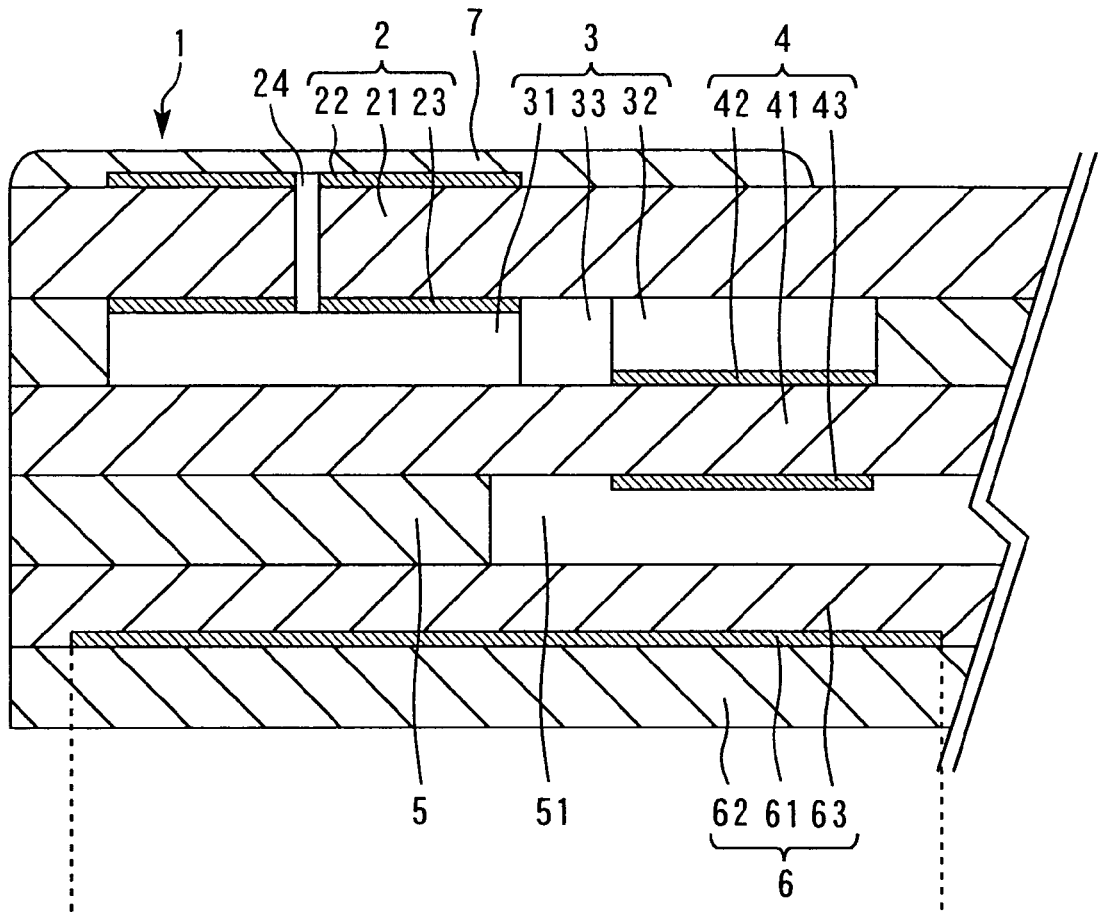
FIGS. 12A and 12B are diagrams illustrating the configuration of a NOx sensor 1 according to a third embodiment of the present invention.

A third embodiment of the present invention will now be described with reference to FIGS. 12A and 12B. The first embodiment, which has been described earlier, forms an activity judgment about the NOx sensor 1 when an inflection point appears in the NOx sensor cell output. Therefore, a NOx sensor cell output whose inflection point is easily locatable should preferably be acquired.

As such being the case, the third embodiment will be described with particular reference to the configuration of the NOx sensor 1 that makes it easy to locate an inflection point in the NOx sensor cell output. FIGS. 12A and 12B are diagrams illustrating the configuration of the NOx sensor 1 according to the third embodiment. More specifically, FIG. 12A is a cross-sectional view of the NOx sensor 1, whereas FIG. 12B is a top view of the heater electrode 61 in the NOx sensor 1.

Figure 12B:
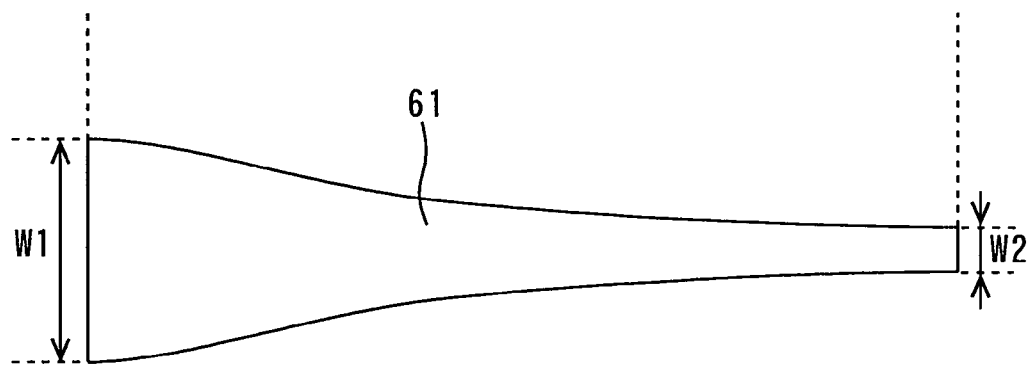

As shown in FIG. 12B, the width W1 of the heater electrode 61 on the side toward the oxygen pump cell 2 is greater than the width W2 of the heater electrode 61 on the side toward the NOx sensor cell 2. The use of the heater electrode 61, which is structured as mentioned above, supplies a larger amount of heat to the oxygen pump cell 2 than to the NOx sensor cell 4. As a result, the oxygen pump cell 2 can be activated earlier than when the employed heater electrode has a uniform width. In other words, the third embodiment provides a greater activity difference between the oxygen pump cell 2 and NOx sensor cell 4 than the first embodiment. This sharpens the fall in the NOx sensor cell output between time t4 and time t5, which is shown in FIG. 2. Therefore, the inflection point in the NOx sensor cell output can be accurately located. This makes it possible to accurately determine the time at which the NOx sensor cell 4 begins to detect the NOx concentration without being affected by the remaining oxygen.

(Modification)

A modification of the third embodiment will now be described with reference to FIG. 13. The third embodiment, which has been described above, is designed so that the heater electrode 61 supplies a larger amount of heat to the oxygen pump cell 2 than to the NOx sensor cell 4.

Figure 13:
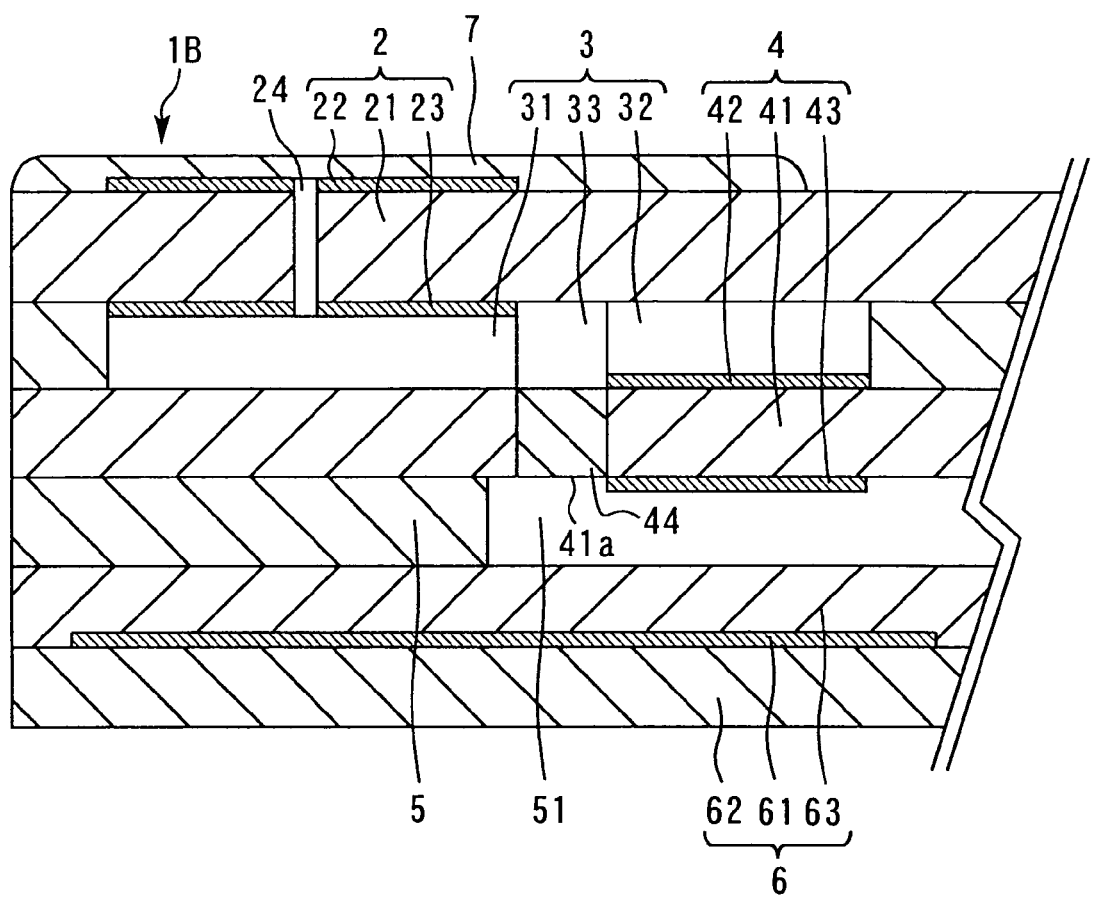
FIG. 13 is a cross-sectional view illustrating a NOx sensor 18 according to a modification of the third embodiment of the present invention.

FIG. 13 is a cross-sectional view illustrating a NOx sensor 1B according to a modification of the third embodiment. As shown in FIG. 13, a portion 41a of the solid electrolyte body 41 that is positioned below the communication hole 33 has a partitioning member 44 for thermal conductivity reduction. More specifically, the partitioning member 44 has a lower thermal conductivity than the solid electrolyte body 41. Therefore, the oxygen pump cell 2 consumes a larger amount of heat than the NOx sensor cell 4. Consequently, the modification of the third embodiment can accurately locate an inflection point in the NOx sensor output as is the case with the third embodiment, which has been described earlier. This makes it possible to accurately determine the time at which the NOx sensor cell 4 begins to detect the NOx concentration without being affected by the remaining oxygen.

Further, enlarging the diameter of the pinhole 24 makes it easy for the exhaust gas to enter the first internal space 31 and makes it easy for the remaining oxygen to leave the first internal space 31. This makes it possible to sharpen the fall in the NOx sensor cell output and locate an inflection point in the NOx sensor cell output with ease.

Fourth Embodiment

A fourth embodiment of the present invention will now be described with reference to FIGS. 14 to 19. The gas concentration detection apparatus according to the fourth embodiment is implemented when the hardware configuration shown in FIG. 1 is employed to let the ECU 8 execute a later-described routine shown in FIG. 19.

[Features of Fourth Embodiment]

As described in conjunction with the first embodiment, it is possible to grasp that the oxygen remaining in the first and second internal spaces 31, 32 before the warm-up of the NOx sensor 1 is substantially removed at the time at which an inflection point appears. Therefore, after the time of inflection point appearance, the NOx sensor cell 4 can detect the NOx concentration without being affected by the remaining oxygen.

However, the NOx sensor cell output is affected not only by the remaining oxygen but also by the state of oxidation of the first detection electrode 42 in the NOx sensor cell 4. The first detection electrode 42 oxidizes because the oxygen remaining in the second internal space 32 reacts with the first detection electrode 42 while the engine is shut down and allowed to stand in the resulting state (during a soak). Oxidation easily progresses particularly when the first detection electrode 42 contains rhodium (Rh).

The oxidized first detection electrode 42 progressively becomes reduced as the warm-up of the NOx sensor 1 progresses. Therefore, the NOx sensor cell output may be varied by the oxygen that is desorbed during the reduction reaction. This may result in failure to detect the NOx concentration with high accuracy. In the above-mentioned electrode containing rhodium (Rh) in particular, it takes a considerable amount of time for oxidized rhodium to become reduced.

Therefore, the failure to achieve accurate NOx concentration may persist over a long period of time.

Figure 14:
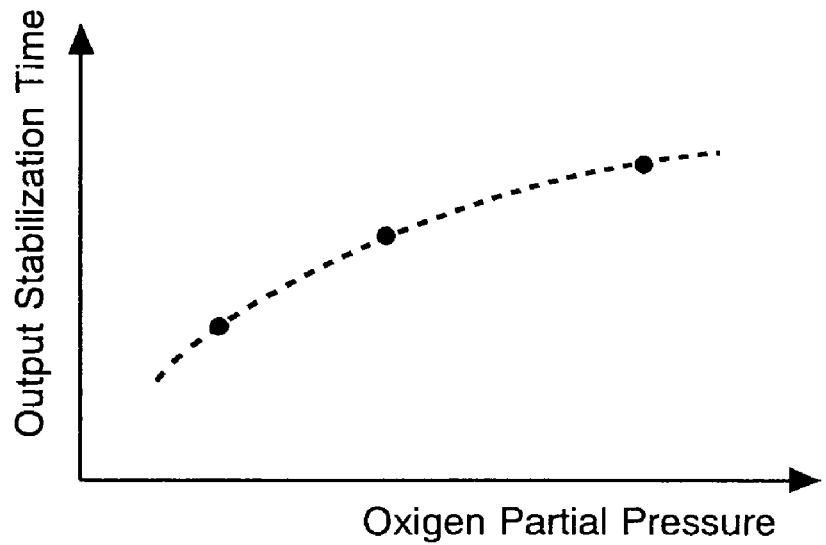
FIG. 14 is a diagram illustrating the relationship between sensor output stabilization time and the oxygen partial pressure around a first detection electrode 42 during a soak.

In other words, variation is based on the state of oxidation of the first detection electrode 42 in the NOx sensor 1 during the interval between the instant at which the inflection point appears and the instant at which the NOx sensor cell output stabilizes (hereinafter referred to as the "output stabilization time"), that is, the instant at which the influence of the oxidation of the first detection electrode 42 is eliminated. FIG. 14 is a diagram illustrating the relationship between the sensor output stabilization time and the oxygen partial pressure around the first detection electrode 42 during a soak. As is obvious from the figure, the higher the oxygen partial pressure in the second internal space 32 during a soak becomes, the longer the output stabilization time is. More specifically, the higher the oxygen partial pressure in the second internal spade 32 becomes, the higher the degree of oxidation of the first detection electrode is. Thus, the time required for reduction reaction completion in the first detection electrode 42 increases. As a result, the output stabilization time becomes prolonged.

Figure 15:
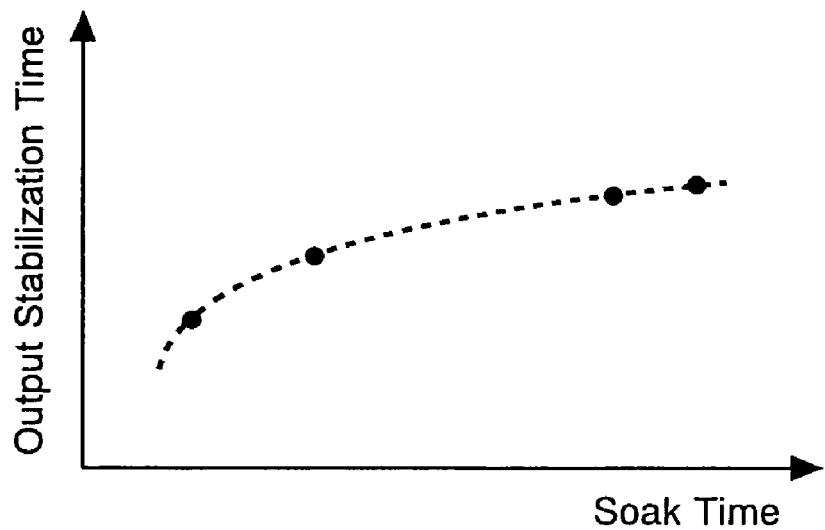
FIG. 15 is a diagram illustrating the relationship between soak time and sensor output stabilization time.

FIG. 15 is a diagram illustrating the relationship between soak time and sensor output stabilization time. As is obvious from the figure, the longer the soak time is, the longer the output stabilization time becomes. It means that the longer the soak time is, the higher the degree of oxidation of the first detection electrode 42 becomes. Therefore, the time required for reduction reaction completion in the first detection electrode 42 increases. Consequently, the output stabilization time becomes prolonged.

As described above, the output stabilization time varies with the oxidation of the first detection electrode 42. As such being the case, the fourth embodiment estimates the state of oxidation of the first detection electrode 42 and makes corrections to eliminate the influence of oxidation of the first detection electrode 42 from the NOx sensor cell output. This makes it possible to accurately detect the NOx concentration by using the NOx sensor cell output generated after inflection point appearance. An oxidation estimation operation and a NOx sensor cell output correction operation will be described in detail below.

(Oxidation Estimation Operation)

Figure 16:
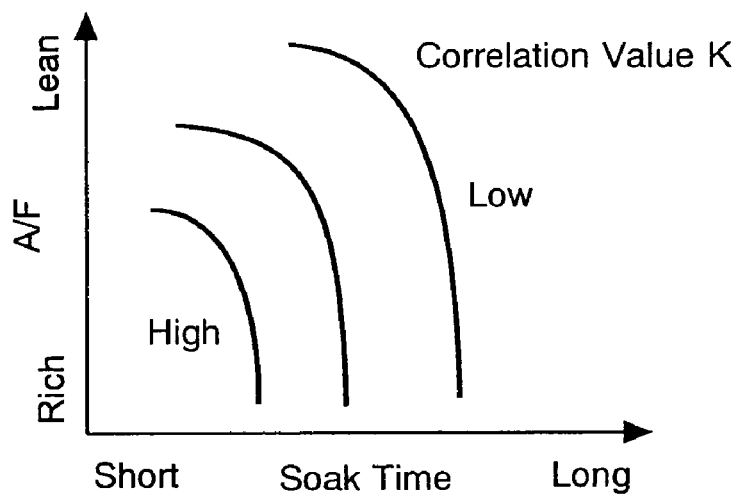
FIG. 16 shows a map for determining the state of oxidation of the first detection electrode 42.
Figure 17:
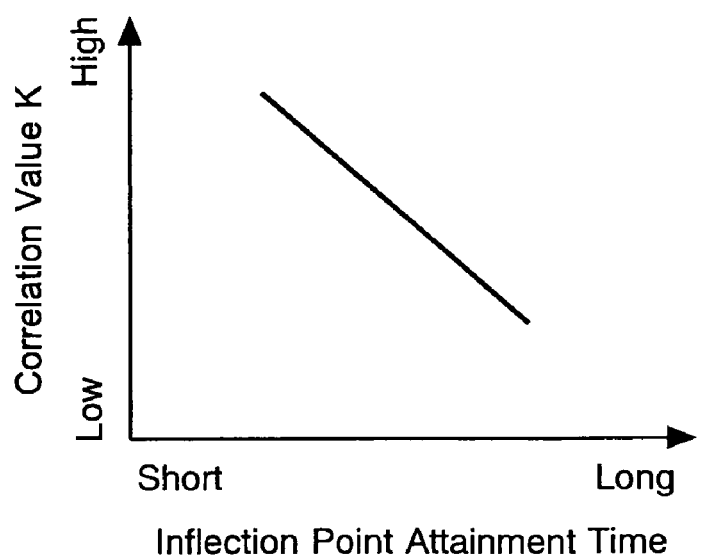
FIG. 17 shows a map for determining the state of oxidation of the first detection electrode 42.

An operation performed to estimate the electrode oxidation of the NOx sensor cell 4 will now be described with reference to FIGS. 16 and 17. As mentioned earlier, in the first detection electrode 42 during a soak, the higher the oxygen partial pressure in the second internal space 32 is or the longer the soak time is, the higher the state of oxidation becomes. FIG. 16 shows a map for determining the state of oxidation of the first detection electrode 42. A correlation value K in which the state of oxidation of the first detection electrode 42 is reflected decreases with an increase in the state of oxidation. Therefore, the correlation value K is determined in accordance with the map shown in FIG. 16, for example. More specifically, the correlation value K decreases with an increase in the soak time. Further, the correlation value K decreases with an increase in the leanness of the air-fuel ratio prevailing during engine shutdown, that is, the air-fuel ratio of the exhaust gas remaining in the second internal space 32. As described above, when the correlation value K concerning the state of oxidation is determined in accordance with the map shown in FIG. 16, the state of oxidation can be reflected in the correlation value K in consideration of a situation in which the first detection electrode 42 is placed during a soak period.

The correlation value K concerning the state of oxidation can also be estimated in accordance with the NOx sensor cell output generated after the start of NOx sensor warm-up. FIG. 17 shows a map for determining the state of oxidation of the first detection electrode 42. In this figure, the horizontal axis represents the interval between the instant at which the NOx sensor 1 begins to warm up and the instant at which an inflection point appears in the NOx sensor cell output (this interval is hereinafter referred to as the "inflection point attainment time"). The longer the inflection point attainment time is, the larger the amount of oxygen remaining in the first and second internal spaces 31, 32 becomes. Therefore, it can be judged that the state of oxidation of the first detection electrode 42 increases with an increase in the inflection point attainment time. Consequently, the correlation value K decreases with an increase in the inflection point attainment time as indicated in the figure.

The correlation value K concerning the state of oxidation can be estimated by combining the above-described methods or by using an alternative method. For example, an integrated value of the NOx sensor cell output that is reached before the inflection point may be used instead of the above-described inflection point attainment time. Another alternative would be to estimate the correlation value K in accordance with the NOx sensor cell output or the ratio between the rate of increase and the rate of decrease in the NOx sensor cell output.

(NOx Sensor Cell Output Correction Operation)

An operation performed to correct the NOx sensor cell output will now be described with reference to FIG. 18. As described earlier, the correlation value K in which the state of oxidation of the first detection electrode 42 is reflected can be estimated in accordance with the soak or inflection point attainment time. As such being the case, the fourth embodiment uses the correlation value K concerning the state of oxidation to correct the NOx sensor cell output N prevailing after the inflection point. More specifically, Equation (3) below is used to calculate the output difference Nm between the NOx sensor cell output Nb prevailing at the inflection point and the NOx concentration estimated at the inflection point (hereinafter referred to as the "estimated NOx value") Np. The estimated NOx value Np can be determined in accordance, for instance, with the engine operating status (intake air amount, EGR amount, etc.) prevailing at the inflection point.

$$Nm=Nb-Np \tag{3}$$

Next, Equation (4) below is used to calculate a final NOx sensor cell output correction value Na for the purpose of correcting the influence of the output difference Nm at the inflection point.

$$Na=N-(Nm-Kt) \tag{4}$$

The correction term (Nm−Kt) in Equation (4) above is obtained by causing a temporal change in the oxidation of the first detection electrode 42 to be reflected in the output difference Nm. In other words, the higher the state of oxidation of the first detection electrode 42 is, the longer the output stabilization time becomes. Therefore, Equation (4) is such that the state of attenuation of the above correction term decreases with a decrease in the correlation value K concerning the state of oxidation. This makes it possible to effectively correct the influence of oxidation of the first detection electrode 42, which is superimposed on the NOx sensor cell output N generated after the inflection point.

Figure 18:
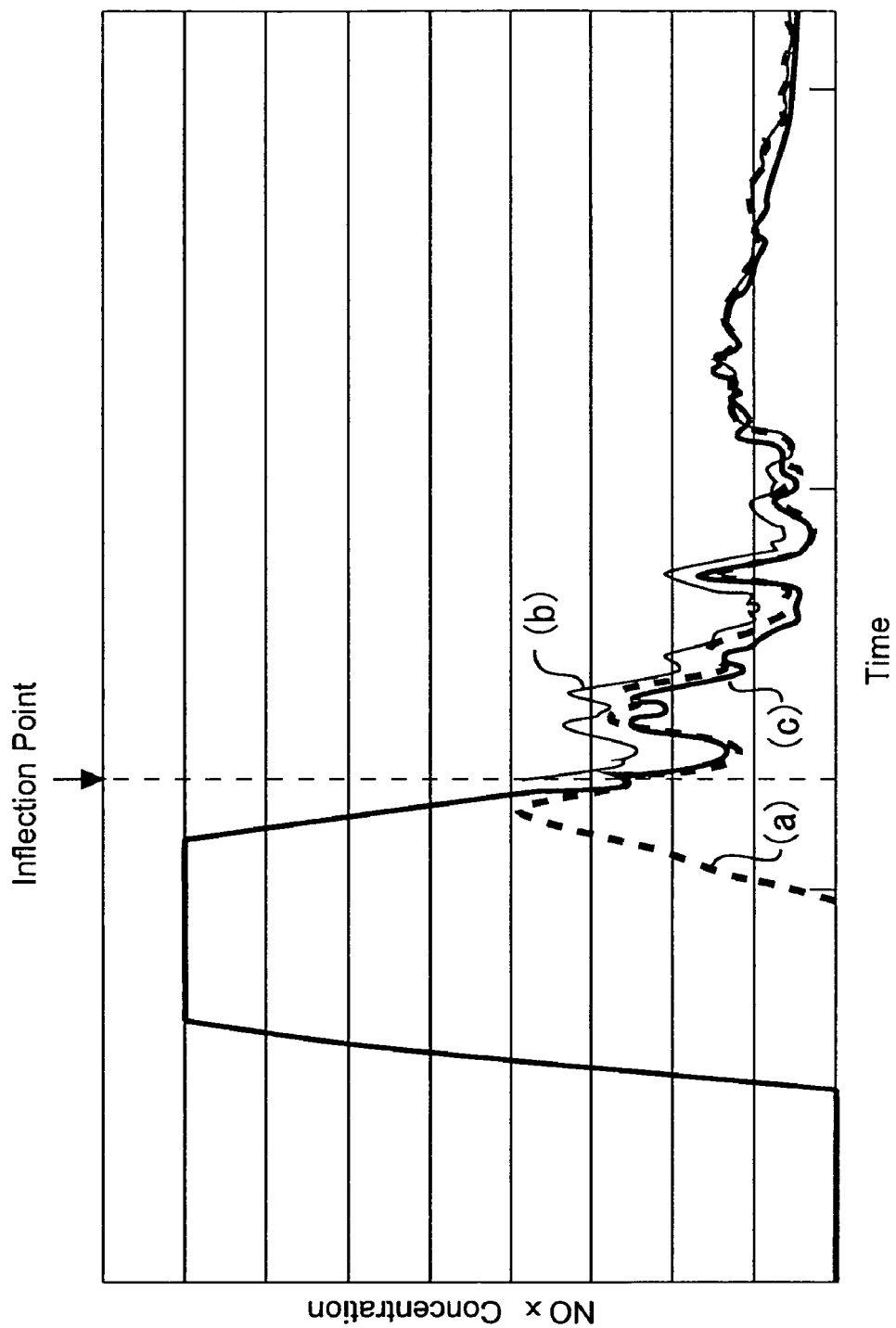
FIG. 18 is a diagram illustrating a comparison between an uncorrected NOx concentration and a corrected NOx concentration.

FIG. 18 is a diagram illustrating a comparison between an uncorrected NOx concentration and a corrected NOx concentration. A broken line (a) indicates the actual NOx concentration in the measurement target gas. A thin line (b) indicates an uncorrected NOx concentration detection value. A thick line (c) indicates a corrected NOx concentration detection value. As is obvious from the figure, the corrected NOx concentration detection value is closer to the actual NOx concentration than the uncorrected NOx concentration detection value.

When the correction term (Nm−Kt) in Equation (4) is not greater than zero (0), it can be estimated that the NOx sensor cell 4 is steadily detecting the NOx sensor cell output N. Such a steady detection period is referred to as the stability time. Thus, the above correction terminates when (Nm−Kt)≦0. This makes it possible to effectively avoid a situation where unnecessary corrections are made to the NOx sensor cell output N.

[Details of Process Performed by Fourth Embodiment]

Figure 19:
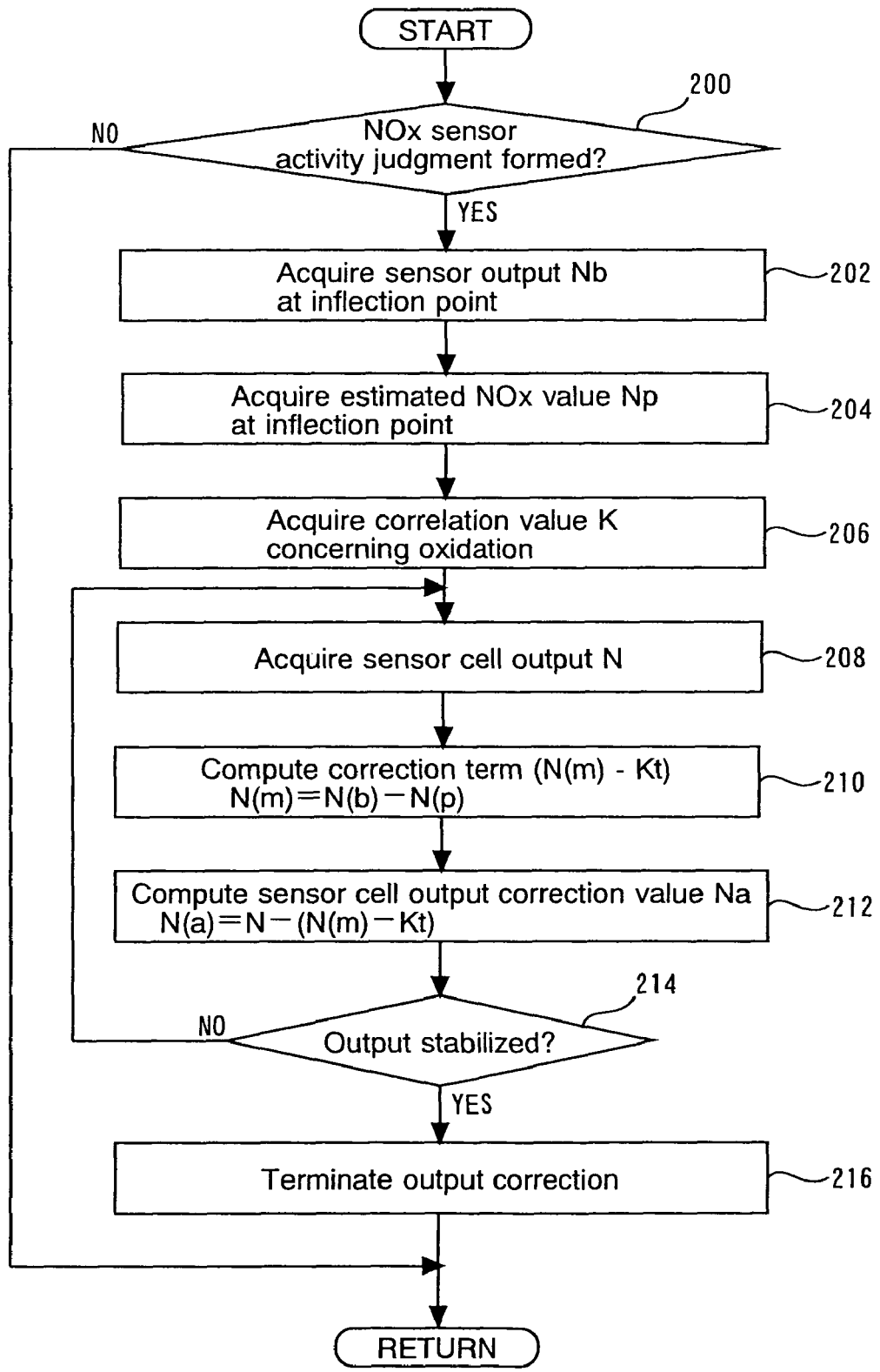
FIG. 19 is a flowchart illustrating a routine that the ECU 8 executes in accordance with a fourth embodiment of the present invention.

A process performed by the fourth embodiment will now be described in detail with reference to FIG. 19. FIG. 19 is a flowchart illustrating a routine that the ECU 8 executes in accordance with the fourth embodiment to correct the NOx sensor cell output N. The routine starts at predetermined intervals together with the routine shown in FIG. 6. First of all, the routine shown in. FIG. 19 executes step 200 to perform an activity judgment process on the NOx sensor 1. More specifically, step 200 is performed to judge whether an activity judgment is formed by the routine shown in FIG. 6, which is executed together with the routine shown in FIG. 19, that is, whether an activity judgment about the NOx sensor 1 is formed in step 112. If the obtained judgment result does not indicate that an activity judgment about the NOx sensor 1 is formed, the routine comes to an immediate end.

If, on the other hand, the judgment result obtained in step 200 indicates that an activity judgment about the NOx sensor 1 is formed, the routine concludes that an inflection point in the NOx sensor output is located, proceeds to the next step (step 202), and acquires the NOx sensor cell output Nb prevailing at the inflection point. More specifically, step 202 is performed to acquire the NOx sensor cell output N(t), which is determined as an inflection point in step 110 of the routine shown in FIG. 6, as the NOx sensor cell output Nb prevailing at the inflection point for the routine shown in FIG. 19.

Next, the routine performs step 204 to acquire an estimated NOx value Np prevailing at the inflection point. More specifically, the estimated NOx value Np of the exhaust gas is determined in accordance with the engine operating status prevailing at the inflection point, that is, in accordance, for instance, with the intake air amount and EGR amount.

Next, the routine performs step 206 to acquire the correlation value K concerning the state of oxidation. More specifically, step 206 is performed to acquire the time interval between the instant at which the engine started and the instant at which the NOx sensor cell output reaches an inflection point, and then determine the correlation value K concerning the state of oxidation in accordance with the map (see FIG. 17) that defines the relationship between the inflection point attainment time and correlation value K.

Next, the routine performs step 208 to acquire the NOx sensor cell output N prevailing after the inflection point. The routine then performs step 210 to compute a correction term for correcting the NOx sensor cell output N acquired in step 208. More specifically, step 210 is performed to substitute the NOx sensor cell output Nb prevailing at the inflection point acquired in step 202 and the estimated NOx value Np acquired in step 204 into Equation (3) and compute the output difference Nm at the inflection point. The correction term (Nm−Kt) is then computed in accordance with the output difference Nm, the correlation value K concerning the state of oxidation that is acquired in step 206, and the elapsed time t from the inflection point.

Next, the routine performs step 212 to compute the NOx sensor cell output correction value Na that prevails t seconds after the inflection point. More specifically, step 212 is performed to substitute the NOx sensor cell output N acquired in step 208 and the correction term (Nm−Kt) acquired in step 210 into Equation (4).

Next, the routine performs step 214 to judge whether the NOx sensor cell output N is stabilized. More specifically, step 214 is performed to judge whether the correction term (Nm−Kt) in Equation (4), which is computed in step 212, is not greater than zero (0). If the obtained judgment result does not indicate that (Nm−Kt)≦0, the routine concludes that the NOx sensor cell output N is still not stabilized, returns to step 208, and acquires the NOx sensor cell output N again.

If, on the other hand, the judgment result obtained in step 214 indicates that (Nm−Kt)≦0, the routine concludes that the NOx sensor cell output N is stabilized, proceeds to step 216, and forcibly terminates the correction made in step 212. Upon completion of step 216, the routine terminates.

As described above, the fourth embodiment can effectively correct the influence of oxidation of the first detection electrode 42, which is superimposed on the NOx sensor cell output N generated after the inflection point. Therefore, it is possible to fulfill the demand for early activation of the NOx sensor 1.

Further, when it is concluded that the NOx sensor cell output N is stabilized, the fourth embodiment, which has been described above, forcibly terminates the operation performed to correct the NOx sensor cell output. This makes it possible to effectively avoid a situation where the NOx sensor cell output deviates from normal due to unnecessary output corrections.

Meanwhile, the fourth embodiment, which has been described above, uses the inflection point attainment time to determine the correlation value K concerning the state of oxidation. However, the present invention is not limited to the use of such a method of determining the correlation value K. For example, the correlation value K may alternatively be determined in accordance with the status of the above-mentioned soak, that is, the air-fuel ratio of the exhaust gas remaining in the NOx sensor 1 during the soak and the soak time. Further, the above-mentioned methods may be combined to achieve the intended purpose. Another alternative would be to determine the correlation value K in accordance, for instance, with an integrated value of the NOx sensor cell output that is reached before the inflection point, the NOx sensor cell output, the ratio between the rate of increase and the rate of decrease in the NOx sensor cell output, or the output of the oxygen pump cell 2 instead of the above-described inflection point attainment time. If the level of accuracy demanded by the system is low, a constant may be used as the correlation value K.

In the fourth embodiment, which has been described above, the oxygen pump cell 2 corresponds to the "oxygen pump cell" according to the first aspect of the present invention; the NOx sensor cell 4 corresponds to the "gas concentration detection cell" according to the first aspect of the present invention; the first detection electrode 42 corresponds to the "gas side electrode" according to the eighth aspect of the present invention; the second detection electrode 43 corresponds to the "atmosphere side electrode" according to the eighth aspect of the present invention; the solid electrolyte body 41 corresponds to the "electrolyte layer" according to the eighth aspect of the present invention; and the NOx sensor cell output corresponds to the "cell output" according to the eighth aspect of the present invention. The "acquisition means" according to the first aspect of the present invention is implemented when the ECU 8 performs step 110; the "gas concentration detection means" according to the eighth aspect of the present invention is implemented when the ECU 8 performs step 208; the "oxidation estimation means" according to the eighth aspect of the present invention is implemented when the ECU 8 performs step 206; and the "correction means" according to the eighth aspect of the present invention is implemented when the ECU performs step 212.

Further, in the fourth embodiment, which has been describe above, the NOx sensor cell output Nb corresponds to the "inflection point concentration detection value" according to the ninth aspect of the present invention; and the estimated NOx value Np corresponds to the "inflection point concentration estimation" according to the ninth aspect of the present invention. The "gas concentration estimation means" according to the ninth aspect of the present invention is implemented when the ECU 8 performs step 204.

Furthermore, in the fourth embodiment, which has been describe above, the output difference Nm corresponds to the "deviation" according to the tenth aspect of the present invention; and the "correction value computation means" according to the tenth aspect of the present invention is implemented when the ECU 8 performs step 210.

Moreover, in the fourth embodiment, which has been describe above, the "stability time estimation means" according to the thirteenth aspect of the present invention is implemented when the ECU 8 performs step 214; and the "prohibition means" according to the thirteenth aspect of the present invention is implemented when the ECU 8 performs step 216.

Fifth Embodiment

[Features of Fifth Embodiment]

The fourth embodiment, which has been described above, corrects the influence of oxidation of the first detection electrode 42 to improve the accuracy of NOx concentration that prevails after an inflection point appears in the NOx sensor cell output. To enhance the accuracy of NOx concentration, therefore, it is preferred that the state of oxidation of the first detection electrode 42 be minimized. As such being the case, a fifth embodiment of the present invention exercises control as described below to inhibit the oxidation of the first detection electrode 42.

(Heater Control)

The fifth embodiment improves the heater electrode 61 that is shown in FIG. 1 and described in conjunction with the fourth embodiment. More specifically, the heater electrode 61 according to the fifth embodiment includes a first heater pattern for heating the vicinity of the pump cell 2 and a second heater pattern for heating the vicinity of the NOx sensor cell 4. The heater control means 83 is capable of controlling the first heater pattern and the second heater pattern on an individual basis.

When the engine having the gas concentration detection apparatus 10 configured as described above shuts down, the heater control means 83 is first controlled to decrease the power applied to the second heater pattern of the heater electrode 61. The first detection electrode 42 oxidizes most readily when it is heated to a temperature between approximately 300° C. and 400° C. Therefore, the oxidation of the first detection electrode can be inhibited by lowering the temperature of the first detection electrode instantaneously after engine shutdown.

In addition, power is continuously applied to the first heater pattern of the heater electrode 61. Since this ensures that the oxygen pump cell 2 continuously discharges oxygen, the concentration of oxygen in the first and second internal spaces 31, 32 can be decreased. Consequently, the state of oxidation of the first detection electrode 42 can be effectively inhibited during a soak.

(Air-Fuel Ratio Control)

Further, the fifth embodiment can inhibit the oxidation of the first detection electrode 42 by exercising air-fuel ratio control instead of exercising heater control as described above. More specifically, air-fuel ratio control can be exercised so that the air-fuel ratio is fuel-richer than the normal one when the engine shut down. Exercising such air-fuel ratio control makes it possible to decrease the concentration of oxygen in the first and second internal spaces 31, 32 during a soak, particularly before a temperature decrease in the first detection electrode 42. Consequently, the state of oxidation of the first detection electrode 42 can be effectively inhibited.

Further, when a gasoline engine equipped with a variable valve train is used, the fifth embodiment controls the variable valve train during engine shutdown so as to open an exhaust valve during a compression stroke. This increases the amounts of unburned gases contained in the exhaust gas. These unburned gases combine with oxygen in an exhaust system and burn. Therefore, the concentration of oxygen in the exhaust gas reaching the gas concentration detection apparatus 10 can be effectively decreased. In addition, when a direct injection engine is employed, the amounts of burned gases contained in the exhaust gas can be increased by performing fuel injection during an exhaust stroke. Consequently, the same advantages are obtained as in a case where the variable valve train is controlled as described above.

In the fifth embodiment, which has been described above, the "oxidation inhibition means" according to the nineteenth aspect of the present invention is implemented when the ECU 8 exercises heater control as described above; and the "oxidation inhibition means" according to the twentieth aspect of the present invention is implemented when the ECU 8 exercises air-fuel ratio control as described above.

The invention claimed is:

1. A gas concentration detection apparatus comprising:
an oxygen pump cell for discharging excess oxygen from a measurement target gas in accordance with voltage application;
a gas concentration detection cell for detecting the concentration of a specific gas component in the gas from which the excess oxygen is discharged by the oxygen pump cell, and outputting a current value according to the detected concentration;
acquisition means which, when the oxygen pump cell and the gas concentration detection cell are being warmed up and when excess oxygen is being discharged, acquires the time at which an inflection point appears in the output of the gas concentration detection cell; and
activity judgment means which regards the time acquired by the acquisition means at which the inflection point appears as an activity time of the gas concentration detection cell.

2. The gas concentration detection apparatus according to claim 1, wherein the acquisition means includes change amount calculation means for calculating the amount of change in the output of the gas concentration detection cell at predetermined time intervals, and acquires, in accordance with a comparison between a reference value and the change amount calculated by the change amount calculation means, the time at which the inflection point appears.

3. The gas concentration detection apparatus according to claim 1, wherein the acquisition means includes change amount calculation means for calculating the amount of change in the output of the gas concentration detection cell at predetermined time intervals, and acquires, in accordance with a change in the change amount calculated by the change amount calculation means, the time at which the inflection point appears.

4. The gas concentration detection apparatus according to claim 1, wherein the acquisition means acquires the time at which the inflection point appears as the time at which the output of the gas concentration detection cell is equal to or smaller than a reference value.

5. The gas concentration detection apparatus according to claim 1, wherein the oxygen pump cell outputs a current value according to the amount of excess oxygen to be discharged; and wherein the acquisition means considers the correlation between the output of the oxygen pump cell and the output of the gas concentration detection cell, and estimates, in accordance with a change in the output of the oxygen pump cell, the time at which the inflection point appears in the output of the gas concentration detection cell.

6. The gas concentration detection apparatus according to claim 5, wherein the acquisition means acquires the time at which an inflection point appears in the output of the oxygen pump cell, and estimates, in accordance with the acquired time, the time at which the inflection point appears in the output of the gas concentration detection cell.

7. The gas concentration detection apparatus according to claim 1, further comprising:
   an air-fuel ratio detection cell which outputs a current value according to an air-fuel ratio of the measurement target gas;
   wherein the acquisition means considers the correlation between the output of the air-fuel ratio detection cell and the output of the gas concentration detection cell, and estimates, in accordance with a change in the output of the air-fuel ratio detection cell, the time at which an inflection point appears in the output of the gas concentration detection cell.

8. The gas concentration detection apparatus according to claim 1, wherein the gas concentration detection cell includes a gas side electrode, which is exposed to the gas from which excess oxygen is discharged by the oxygen pump cell; an atmosphere side electrode, which is exposed to atmospheric air; and an electrolyte layer, which is positioned between the gas side electrode and the atmosphere side electrode to permit the movement of oxygen ions between the electrodes; the gas concentration detection apparatus further comprising:
   gas concentration detection means for detecting the concentration of a specific gas component in accordance with a cell output of the gas concentration detection cell, the cell output prevailing after the time at which the inflection point appears;
   oxidation estimation means for estimating a state of oxidation of the gas side electrode; and
   correction means for correcting the influence of oxygen reduced from the gas side electrode upon the cell output in accordance with the state of oxidation.

9. The gas concentration detection apparatus according to claim 8, further comprising:
   gas concentration estimation means for estimating the concentration of a specific gas component in accordance with the operating status of an internal combustion engine;
   wherein the correction means corrects the cell output in accordance with an inflection point concentration detection value, an inflection point concentration estimation and the state of oxidation, the inflection point concentration detection value being determined by the gas concentration that prevails at the inflection point and the inflection point concentration detection value being detected by the gas concentration detection means, the inflection point concentration estimation being determined by the gas concentration that prevails at the inflection point and the inflection point concentration estimation being estimated by the gas concentration estimation means.

10. The gas concentration detection apparatus according to claim 9, wherein the correction means includes correction value computation means for computing a correction value in which the influence of the state of oxidation and the elapsed time from the time at which the inflection point appears is reflected in a deviation between the inflection point concentration detection value and the inflection point concentration estimation, and corrects the cell output by subtracting the correction value from the cell output.

11. The gas concentration detection apparatus according to claim 10, wherein the correction value computation means performs computations so that the correction value decreases with an increase in the elapsed time.

12. The gas concentration detection apparatus according to claim 10, wherein the correction value computation means performs computations so that the correction value increases with an increase in the oxidation.

13. The gas concentration detection apparatus according to claim 10, further comprising:
   stability time estimation means for estimating a stability time, the stability time being the time at which the gas concentration detection cell detects the cell output on which the influence of oxidation of the gas side electrode is not superimposed; and
   prohibition means for prohibiting the correction means from being executed with respect to the cell output prevailing at the stability time.

14. The gas concentration detection apparatus according to claim 13, wherein the stability time estimation means estimates the stability time as the time at which the correction value is 0 or smaller.

15. The gas concentration detection apparatus according to claim 8, wherein the state of oxidation estimated by the oxidation estimation means increases with an increase in the interval between the instant at which the gas concentration detection cell becomes energized and the instant at which the inflection point appears.

16. The gas concentration detection apparatus according to claim 8, further comprising:
   integrated value computation means for computing the integrated value of the cell output that is reached during the interval between the instant at which the gas concentration detection cell becomes energized and the instant at which the inflection point appears;
   wherein the state of oxidation estimated by the oxidation estimation means increases with an increase in the integrated value.

17. The gas concentration detection apparatus according to claim 8, wherein the oxidation estimation means includes air-fuel ratio acquisition means for acquiring the air-fuel ratio of the measurement target gas that prevailed the last time the internal combustion engine shut down; and wherein the state of oxidation estimated by the oxidation estimation means increases with an increase in the leanness of the air-fuel ratio.

18. The gas concentration detection apparatus according to claim 8, wherein the oxidation estimation means includes standing time acquisition means for acquiring a standing time, that is, the interval between the last internal combustion engine shutdown and the current internal combustion engine start; and wherein the state of oxidation estimated by the oxidation estimation means increases with an increase in the standing time.

19. The gas concentration detection apparatus according to claim 8, further comprising:
   oxidation inhibition means for inhibiting the oxidation of the gas side electrode during internal combustion engine shutdown.

20. The gas concentration detection apparatus according to claim 19, wherein the oxidation inhibition means exercises control to enrich the air-fuel ratio when the internal combustion engine shut down.

21. A gas concentration detection apparatus comprising:
   excess oxygen removal means for removing excess oxygen from a measurement target gas;
   a gas concentration detection cell for detecting the concentration of a specific gas component in the gas from which the excess oxygen is removed by the excess oxygen removal means; and
   activity judgment means which, when the excess oxygen removal means and the gas concentration detection cell are being warmed up and when excess oxygen is being removed, regards the time at which an inflection point appears in the concentration of the specific gas component detected by the gas concentration detection cell as an activity time of the gas concentration detection cell.

22. A gas concentration detection apparatus comprising:
   an oxygen pump cell for discharging excess oxygen from a measurement target gas in accordance with voltage application;
   a gas concentration detection cell for detecting the concentration of a specific gas component in the gas from which the excess oxygen is discharged by the oxygen pump cell, and outputting a current value according to the detected concentration;
   acquisition device which; when the oxygen pump cell and the gas concentration detection cell are being warmed up and when excess oxygen is being discharged, acquires the time at which an inflection point appears in the output of the gas concentration detection cell; and
   activity judgment device which regards the time acquired by the acquisition device at which the inflection point appears as an activity time of the gas concentration detection cell.
the gas concentration detection cell.

* * * * *